US009833560B2

(12) United States Patent
Reichert et al.

(10) Patent No.: US 9,833,560 B2
(45) Date of Patent: Dec. 5, 2017

(54) IV SET SYSTEM WITH BYPASS MANIFOLD

(71) Applicant: Somnus Medical, LLC, Pleasant Grove, UT (US)

(72) Inventors: Lucas Reichert, Roosevelt, UT (US); Edwin T. Bulloch, Vernal, UT (US); Anthony Clark Harward, Provo, UT (US)

(73) Assignee: Somnus Medical, LLC, Roosevelt, UT (US)

( * ) Notice: Subject to any disclaimer, the term of this patent is extended or adjusted under 35 U.S.C. 154(b) by 482 days.

(21) Appl. No.: 14/458,229

(22) Filed: Aug. 12, 2014

(65) Prior Publication Data
US 2015/0040988 A1 Feb. 12, 2015

Related U.S. Application Data

(60) Provisional application No. 61/864,977, filed on Aug. 12, 2013.

(51) Int. Cl.
*A61M 5/14* (2006.01)
*A61M 5/168* (2006.01)
(Continued)

(52) U.S. Cl.
CPC ........ *A61M 5/1413* (2013.01); *A61M 5/1408* (2013.01); *A61M 5/16813* (2013.01);
(Continued)

(58) Field of Classification Search
CPC ............. A61M 5/1413; A61M 5/1408; A61M 5/16813; A61M 5/16881; A61M 39/10;
(Continued)

(56) References Cited

U.S. PATENT DOCUMENTS 3,696,920 A   10/1972 Lahay
4,105,029 A    8/1978 Virag
(Continued)

FOREIGN PATENT DOCUMENTS

WO   WO 2006/014320 A2   2/2006

OTHER PUBLICATIONS

Hart, "Necessity Giving Birth to Range of Inventions", www.colorsafeivlines.com/press-release/, Jan. 2, 2011, pp. 3, Guerneville, CA.

(Continued)

*Primary Examiner* — Manuel Mendez

(57) ABSTRACT

An intravenous (IV) set system comprising a primary IV set defining a primary flow line of the IV set system. The primary flow line can include multiple access points along its length and feeds to a merging fluid pathway proximate to the distal terminus of the primary IV set. At least one secondary IV set with corresponding flow lines can be separably joined to the primary IV set to cause the secondary flow lines to be in fluid communication with the primary flow line. At least one of the IV sets can have a unique set of uniform marking indicia to facilitate rapid identification of the IV sets from other IV sets within the IV set system. Such marked and identified primary and/or secondary IV sets can be allocated to specific medical functions and/or can be for use by specific medical personnel to thereby minimize risk of error in administration of an IV to a patient. The IV set system can further comprise a merging fluid pathway about a primary IV set.

30 Claims, 10 Drawing Sheets

(51) Int. Cl.
*A61M 39/10* (2006.01)
*A61M 39/28* (2006.01)

(52) U.S. Cl.
CPC ........ *A61M 5/16881* (2013.01); *A61M 39/10* (2013.01); *A61M 39/287* (2013.01); *A61M 2039/1088* (2013.01); *A61M 2205/6018* (2013.01); *A61M 2205/6063* (2013.01); *Y10T 137/0318* (2015.04); *Y10T 137/8158* (2015.04); *Y10T 137/86726* (2015.04); *Y10T 137/9029* (2015.04)

(58) Field of Classification Search
CPC ........ A61M 39/287; A61M 2039/1088; A61M 2205/6018; A61M 2205/6063; Y10T 137/8158; Y10T 137/86726; Y10T 137/9029
USPC ............. 137/595, 6–6, 192; 604/251, 30–34, 604/80–83
See application file for complete search history.

(56) References Cited

U.S. PATENT DOCUMENTS

| | | | |
|---|---|---|---|
| 4,114,241 A | 9/1978 | Bisping | |
| 4,219,022 A | 8/1980 | Genese | |
| 4,237,879 A * | 12/1980 | Genese | A61M 5/1408 604/126 |
| 4,298,001 A | 11/1981 | Hargest, III et al. | |
| 4,573,974 A | 3/1986 | Ruschke | |
| 4,654,026 A | 3/1987 | Underwood | |
| 4,734,091 A * | 3/1988 | Boyle | A61F 9/00736 137/883 |
| 5,059,173 A | 10/1991 | Sacco | |
| 5,078,699 A | 1/1992 | Haber | |
| 5,190,525 A * | 3/1993 | Oswald | A61M 5/1408 604/83 |
| 5,207,643 A | 5/1993 | Davis | |
| 5,226,892 A | 7/1993 | Boswell | |
| 5,316,246 A | 5/1994 | Scott et al. | |
| 5,897,526 A | 4/1999 | Vaillancourt | |
| 6,287,608 B1 | 9/2001 | Levin et al. | |
| 6,443,156 B1 | 9/2002 | Niklason et al. | |
| 6,511,456 B1 | 1/2003 | Salinas et al. | |
| 6,780,167 B2 | 8/2004 | Leone | |
| 7,942,371 B1 | 5/2011 | McCoy | |
| 2002/0038392 A1 * | 3/2002 | De La Huerga | A61M 5/14212 710/8 |
| 2003/0130617 A1 | 7/2003 | Leone | |
| 2004/0135039 A1 | 7/2004 | Reichert et al. | |
| 2005/0171492 A1 * | 8/2005 | Rodriquez | A61M 5/14 604/264 |
| 2005/0267404 A1 | 12/2005 | Kraushaar | |
| 2006/0113432 A1 | 6/2006 | Driskell | |
| 2010/0294271 A1 | 11/2010 | Pittaway et al. | |
| 2011/0011395 A1 | 1/2011 | Mazela et al. | |
| 2011/0106054 A1 | 5/2011 | Osborne et al. | |
| 2012/0029479 A1 | 2/2012 | Kraushaar | |
| 2012/0143150 A1 | 6/2012 | Page et al. | |

OTHER PUBLICATIONS

Search Report for International application PCT/US2014/050781 dated Dec. 16, 2014, 16 pages.
Search Report for International application PCT/US2014/050785 dated Dec. 1, 2014, 13 pages.
Search Report for International application PCT/US2014/050786 dated Dec. 1, 2014, 12 pages.
Codan US Corporation, Codan Specialty NICU IV Sets All-In-One Systems Offer Effective Infection Prevention, http://www.codanusa.com/Innovations-Solutions/Specialty-NICU-IV-Sets, to the best of applicant's knowledge article was available before the application filing date, 2 pages, Santa Ana, CA.
Codan US Corporation, Walrus by Codan Specialty Anesthesia Sets and Blood Sets, http://www.codanusa.com/Innovations-Solutions/Walrus-by-CODAN, to the best of applicant's knowledge article was available before the application filing date, 2 pages, Santa Ana, CA.

* cited by examiner

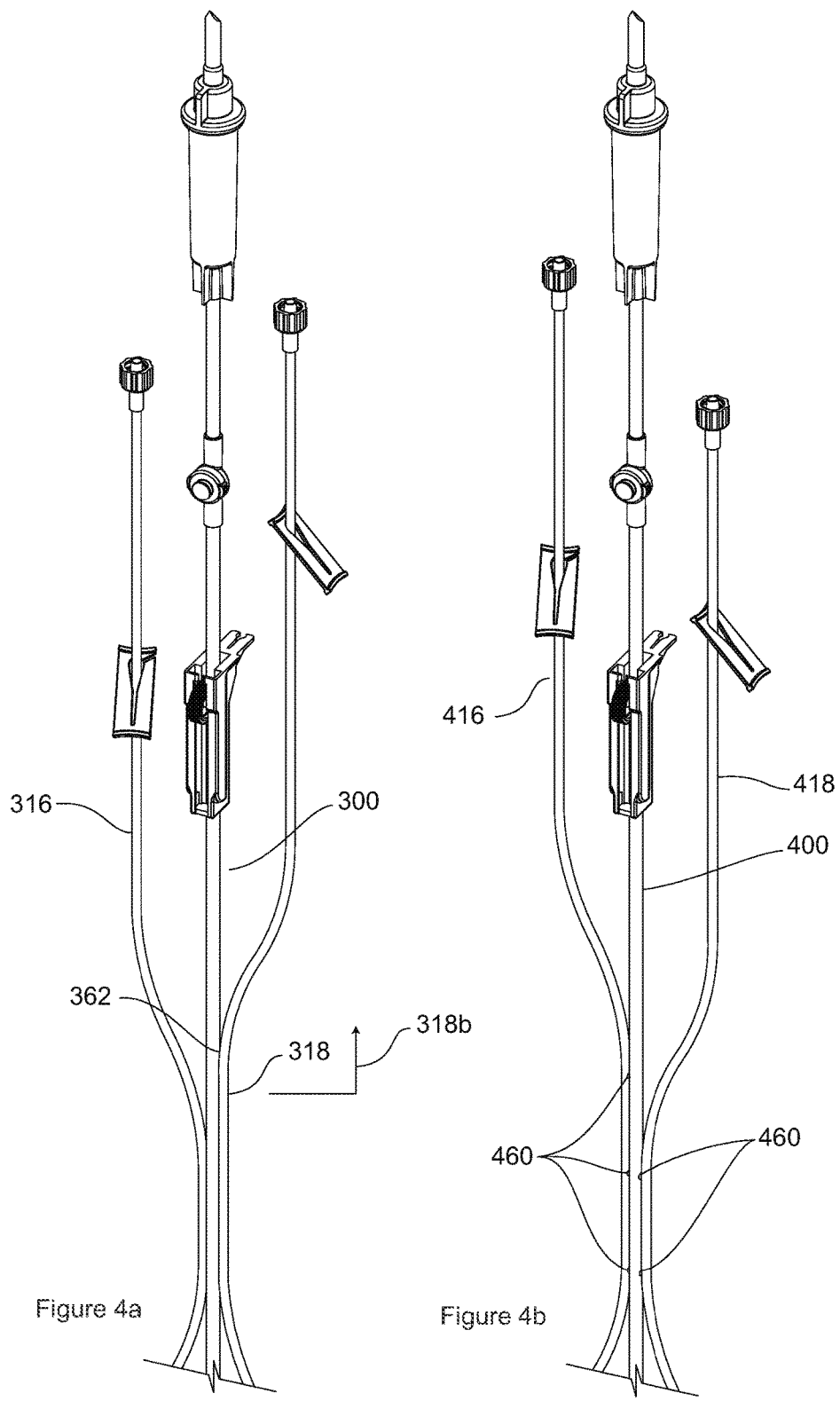

IV SET SYSTEM WITH BYPASS MANIFOLD

RELATED APPLICATIONS

This application claims the benefit of U.S. Provisional Application Ser. No. 61/864,977, filed Aug. 12, 2013, and entitled, "Multiline IV Set With Coded, Strippable Components," which application is incorporated by reference herein in its entirety.

BACKGROUND

One of the major benchmarks of medical care was the introduction of an Intravenous (IV) set to access the circulatory system of a patient, enabling the administration of fluids and medications in a controlled, predictable manner. The typical IV set includes a primary fluid flow line of tubular construction with one or more access points. Some of these access points can comprise access ports that allow the administration of medications through either a syringe by push or by infusion through another IV set (primary or secondary). A primary access point is located at one end of the IV set with a fluid source, such as normal saline or some other carrier fluid. A spike and drip chamber assembly is positioned at a terminus or proximal end of the flow line with means for attachment to a patient injection site on a distal end. Secondary flow lines may be combined with the primary flow line with similar construction options.

Use of sets has now become ubiquitous at every stage of medical care, from the site of an accident or injury, through transport to the hospital, during emergency room and surgical procedures and potentially continuing into the ICU and general hospital care. At each successive stage of procedure or treatment, different medical personnel typically become involved. Normally, later stage medical personnel will not have actual firsthand experience with a patient and the various multiple attached IV sets. Often, they may have to guess as to the purpose and procedure associated with each previous IV set, including what medications may have been administered. Usually, some form of record or identification is written or provided with respect to each IV set, the applied medications, and various details regarding patient care. Usually this is in the form of a medical chart that accompanies the patient, providing a history of such procedures. Unfortunately, there may be confusion as to the specific procedures applied with respect to an IV set based upon lack of proper interpretation or inaccuracy of description.

When multiple medical personnel are involved, the combinations of procedures involving the multiple IV sets become even more complex. This is particularly true with respect to surgical procedures in an operating room. In addition to the surgical staff having to focus on specific medical problems, other personnel may be involved, such as an anesthesia provider who typically administers anesthesia medications via the IV set. From an anesthesia provider's view, one primary concern can involve determining which IV set has the carrier fluid that he/she can use to push any needed medication (i.e., which IV set, including spike/drip chamber, goes directly to the patient).

In the operating room, or during transport to and from the operating room, the anesthesia provider must be prepared and able to quickly modify medication levels as required by hemodynamic changes in the patient's state of being, as well as anesthesia demands and unexpected emergencies. Confusion as to the correct identity of a given IV set can be a serious risk to the patient and a great frustration to attending medical personnel. The general absence of standardized labels, standardized positioning requirements along the IV sets, and inadequate IV port or access identification present an ongoing medical risk.

In addition, there are inherently many basic problems associated with the general use of current IV sets in any given situation. For example, constant concerns exist with respect to the proper introduction of a medication at an access point, the rate of fluid delivery through the flow line, the adequacy of mixture of medications within the IV set(s), the delay in transit time of a particular medication to the injection site, the amount of fluid in the flow line ahead of a newly administered drug, and maintenance of a clean and functional injection site with the patient. When multiple IV sets are combined these various problems are magnified in complexity because of the increased amount of medications and hardware used as part of the compilation of IV sets, as well as the diverse medical personnel monitoring the same compilation of IV sets.

The participation of numerous personnel using the same compilation of IV sets often results in competition for physical access by the user to access ports, control of delivery rates with valves, making modifications in the respective IV sets, etc. Maintaining convenient access to the correct IV set and ensuring proper line identification is the responsibility of each individual attempting to utilize the IV set at the same time, This competition for immediate access by multiple users can add considerable additional stress to an already stressful environment.

These problems take on a new dimension of risk in the more dynamic environment of an operating room, where decisions must be made immediately and acted upon under conditions of great urgency. Each member of the medical team must be assured of quick and certain access to the component IV set(s) associated with his or her area of attention and responsibility. In addition to proper identification of an IV set, each individual most be capable of accessing the access points and other structural aspects of the IV set or compilation of IV sets for administering the required medication or procedure, without interfering with the activities of other medical personnel attending to the patient through the same IV set or compilation of IV sets.

To meet these needs, various temporary and rudimentary methods of identifying individual IV sets and of bundling these together to avoid entanglement have been applied. For example, individual IV sets may be tagged or labeled at a single site by the attending physician or other personnel to identify its purpose. However, there is no standardization of such practices, thus leading to confusion and wasted time spent looking up and down the IV set for identification. Other attempts at line identification have included coloring the actual IV set itself. This may be a problem, however, because medications are often colored themselves. For example, a yellow IV set containing therein a cancer medication that is blue could provide a misrepresentative or false appearance in the form of a green IV set.

To avoid entanglement, the various IV sets may be taped together or otherwise generally clipped into a bundle. This grouping of multiple IV sets with intermittent access ports, however, may become very confusing to multiple users of the compilation of IV sets, and is also very time consuming. Access points allow the various attending personnel to administer medications through a syringe by push or by infusion through an additional IV set. Not only does this additional structure add to the complexity of the compilation of IV sets with respect to possible line entanglement, but it also limits access for the practitioner using a more proximal access port. For example, when a fluid restriction is being observed (e.g., pediatrics, kidney failure, or complex surgery case), pushing a medication through an access point far from the patient becomes a problem. Boluses of fluid must be administered to deliver the medication from the proximal access points to a distal end terminating at the patient.

In view of these ongoing problems, medical personnel continue to make ad hoc adaptations in an effort to mitigate the confusion associated with current IN set practices. Despite these various solutions, current use of IV sets still requires considerable patience and a high degree of attention on the part of medical personnel to deal with the ongoing difficulties associated with such current IV sets. Past improvements in IV set technology seem to have been focused on isolated solutions to distinct or different problems, thus lacking in more general and combined resolutions of such problems, and even creating new issues in some instances.

BRIEF DESCRIPTION OF THE DRAWINGS

Features and advantages of the invention will be apparent from the detailed description which follows, taken in conjunction with the accompanying drawings, which together illustrate, by way of example, features of the invention; and wherein:

FIG. 4a illustrates a partial plan view of an IV set system comprising a plurality of integral inter-attached lines having a strippable property, in accordance with one exemplary embodiment of the present invention;

FIG. 4b illustrates a partial plan view of an IV set system comprising a plurality of integral inter-attached lines having a strippable property, in accordance with another exemplary embodiment;

DETAILED DESCRIPTION

Figure 1:
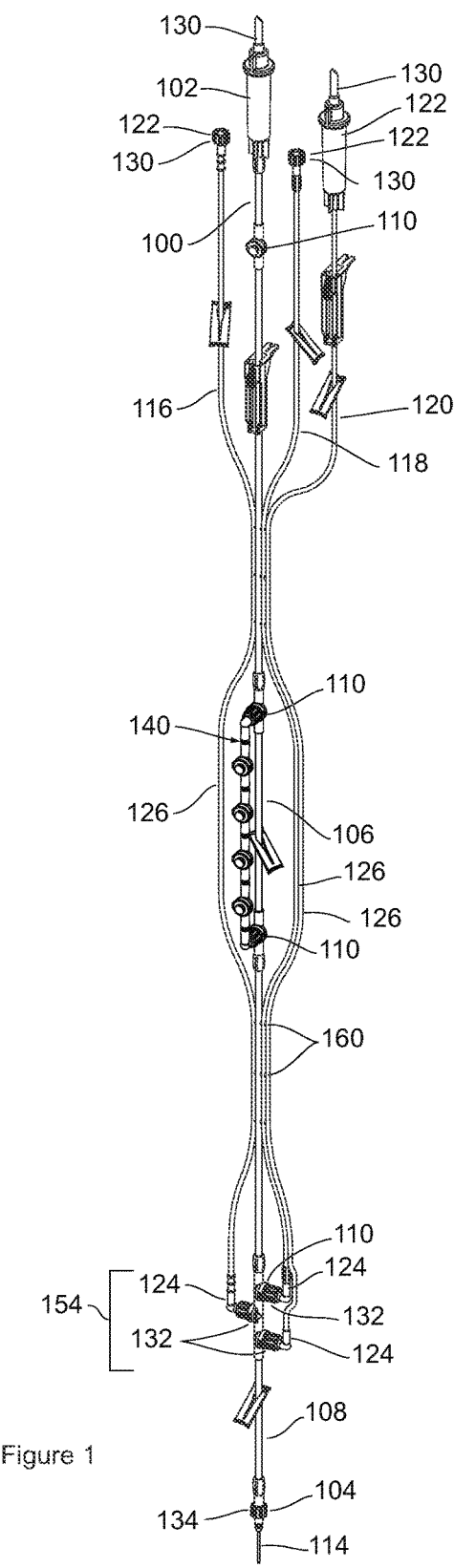
FIG. 1 illustrates a plan view of an IV system in accordance with one exemplary embodiment of the present invention.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

An initial overview of technology embodiments is provided below and then specific technology embodiments are described in summary and in further detail later. This initial summary is intended to aid readers in understanding the technology more quickly, but is not intended to identify key features or essential features of the technology, nor is it intended to limit the scope of the subject matter.

At the outset, an IV set is intended to mean a single IV line. An IV set system is intended to mean at least a plurality of IV sets within the IV set system. The IV set system can comprise additional elements operable within the IV set, such as a merging fluid pathway, a manifold, various access points, etc. An access point is intended to mean any point along the IV set in which access is provided to the fluid flow within the IV set. An access point can include such elements as access ports, spike/drip chambers, patient interconnect structures, fluid interconnect means, etc. An access port is intended to mean a specific type of access point that facilitates access to the fluid flow within the IV set, such as by push (e.g., using a syringe) or by infusion (e.g., through fluid coupling of another IV set).

In considering current IV sets or compilation of IV sets and the evolution of these, the present inventors have noted that isolated and segmented resolution of different perceived problems has failed to address many of the experienced problems discussed above. Indeed, many of the individual solutions created over the past years have contributed to further difficulties in IV set identification and access. Therefore, instead of focusing on one or more isolated problems associated with current IV sets, the present disclosure seeks to provide a more extensive and encompassing solution that addresses a variety of problems associated with current IV sets, such as those discussed above. The present IV set technology, as discussed herein, focuses, without limitation, on meeting fluid delivery requirements, configuring or providing multiple IV sets with indicia to aid in identification both by fluid type and primary user, configuring one or more IV sets within an IV set system to avoid entanglement of flow lines and to improve user access, adapting an IV set with a manifold bypass component for regulating multiple fluid sources within the same IV set, providing a merging fluid pathway and optimizing the position of this, and expanding the methodology of IV set technology to integrate a multi-stage, multi-care venue historical identification aspect.

These design aspects can be incorporated into various methods of use including (i) developing multiple venue utilization capability and progressive records of use for a given IV set or IV set system as the patient progresses through various stages of medical treatment, (ii) providing for retention of certain IV sets, or a link to their indicia, as part of a record of use, while programming deletion of other IV sets having no historical value, and (iii) developing standard protocols within the medical field to expand utility of the IV set as a source of patient treatment information, as well as to further minimize malpractice risks in patient care involving the administration of IV fluids and medications.

Historically, the use of the IV set has been segmented within various progressive stages of the patient experience. For example, at the scene of an accident, paramedics may apply an IV set for temporary relief and application of emergency procedures. Upon arrival at the emergency room, a new IV set may be substituted upon identification of particular needs of the patient. Once the patient is stabilized and an initial diagnosis is made, changes may again be required in the IV set or the now compilation of IV sets. Eventually, the patient may be moved to a hospital ward for further treatment and evaluation. Once again, further modifications may be needed with respect to the patient's IV. If surgery is ultimately required, the patient is typically prepared, which preparations cart include additional modifications in IV set up as needed for delivery of anesthesia and other required medications. Finally, upon completion of the surgery, the compilation of IV sets may again be adapted for normal hospital usage. As such, the reality of changing patient environments and medical needs, coupled with the recognized problems associated with current IV set technology, calls for a dynamic IV set system and solution that can be adapted to meet the numerous requirements of secure and reduced risk administration of IV medications, as well as improved convenience of use for medical personnel.

An IV set system in accordance with some exemplary embodiments of the present invention can comprise a primary IV set having a proximal terminus, a distal terminus, and an intermediate tubular length defining a primary flow line and primary fluid flow path of the primary IV set. The primary flow line can include multiple access points along its length that facilitate access to the fluid pathway of the primary IV set, some of which can comprise access ports. The primary IV set can further comprise a merging fluid pathway proximate to the distal terminus in fluid communication with the fluid flow path and the various access points used to access the fluid flow path.

The IV set system can further comprise at least one secondary IV set having a secondary flow line. The secondary IV set can be removably and fluidly coupled to the primary IV set. For example, the secondary flow line can be secured to the primary flow line. The secondary IV set can also include a proximal terminus; a distal terminus, and an intermediate tubular length. The proximal termini of each of the primary IV set and of the at least one secondary IV set can further include a coupling structure for receiving a fluid source to be coupled to the IV set system for providing at least one fluid medium to a patient through the primary IV set. The distal terminus of the at least one secondary IV set can also include a fluid interconnect of various types and configurations for attaching the distal terminus of the secondary IV sets(s) to the primary IV set, such as via the merging fluid pathway near the distal terminus of the primary IV set. The distal terminus of the primary flow line of the primary IV set can provide a patient interconnect for coupling the primary flow line of the primary IV set to a patient injection site. In accordance with one exemplary aspect of the present invention, the respective proximal terminus, access points, and distal terminus of the primary IV set and each secondary IV set can have a unique set of marking indicia to distinguish them from one another and other secondary flow lines.

The IV set system can further comprise one or more physically connected IV sets. As such, another exemplary aspect of this invention can be to integrally secure at least one secondary IV set to the primary IV set in a parallel relationship in at least a semi-continuous manner substantially along the intermediate tubular length of these. This can function to inhibit line entanglement within the IV set system. Stated differently, at least one secondary IV set can be physically removably coupled to the primary IV set, and/or another secondary IV set, at one or more locations external to the fluid flow paths of each. In other words, the tubular structures making up the respective IV sets and defining the fluid flow paths therein can be physically coupled together along their length. In one aspect, this can be achieved by joining or physically linking the outer surfaces of the respective tubular structures together in a continuous manner. In another aspect, this can be done in a non-continuous manner. Moreover, the physical external connection of two IV sets can be done without interfering with the fluid flow paths of any of the IV sets, This physical connection of the various IV sets within the IV set system is not to be mistaken for the potential fluid connection between various IV sets within the IV set system. Indeed, it will be understood that the secondary IV sets can also be removably fluidly coupled to the primary IV set, such that their fluid flow paths are in communication with one another (i.e., the fluid flow paths can be caused to intersect or otherwise merge or come together).

By being removably physically coupled together, the secured tubular lengths or the secured IV sets can be ideally configured for fully or partially peeling or stripping away from one another in a selectable fashion, such as only when needed or desired. In one example, one or more secondary IV sets can be fully stripped from the primary IV set and discarded if not needed. In another example, secondary IV set(s) can be selectively partially stripped away from the primary IV set as needed or desired to provide variable free lengths of the one or more secondary IV set(s), such as to facilitate fluidly connecting these to the primary IV set and establishing one or more secondary flow lines and corresponding flow paths with respect to the primary flow line and its corresponding flow path.

The primary IV set may also include a manifold device positioned proximate to the distal terminus of the primary IV set and mounted externally to the primary flow line, wherein the manifold can be removably coupled to the primary IV set and configured to be in fluid communication with the primary flow line of the primary IV set. The manifold thus functions as an alternate flow line and corresponding flow path configured to selectively bypass a specific segment of the primary flow line and its corresponding flow path.

A method for utilizing the same IV set system across various stages of patient care associated with applications of multiple IV procedures can comprise the steps of (a) selecting an IV set system having a primary IV set and one or more secondary IV sets integrally connected with the primary line at one or more positions external to the fluid flow path of each; (b) attaching the IV set system to a patient during a first stage of medical care and starting IV flow using at least the primary IV set; and (c) optionally progressing through use of at least one successive stages of medical care, wherein at least one secondary IV set is used in each stage and retained, or whose indicia is retained, as part of the IV set system for later identification of the medical care provided during the respective two successive stages.

A method for providing selective identification of at least one flow line within an intravenous (IV) set system having (i) a primary IV set having a proximal terminus, a distal terminus, and an intermediate tubular length defining a primary flow line of the IV set system, and (ii) at least one secondary IV set defining at least one secondary flow line configured to feed to the primary flow line, the at least one secondary line having a proximal terminus, a distal terminus, and an intermediate tubular length can comprise providing top-level marking indicia on the primary IV set; and providing marking indicia on the secondary IV set different from the top-level marking indicia on the primary IV set. The method can further comprise providing second-level marking indicia on the primary IV set, wherein the second-level marking indicia of the primary IV set matches the marking indicia of the secondary IV set providing a set of matching indicia across IV sets; providing additional second-level marking indicia on the primary IV set, wherein the IV set system further comprises an additional secondary IV set operable with the primary or secondary IV sets, the additional secondary IV set comprising marking indicia that differs from the top-level marking indicia of the primary set and the marking indicia on the secondary IV set; matching the marking indicia on the additional secondary IV set with the additional second-level marking indicia on the primary IV set; associating the second-level marking indicia on the primary IV set with an access point of the primary IV set, and associated the second-level marking indicia on the secondary IV set with an access point of the secondary IV set; and associating the various marking indicia of the primary and secondary IV sets with one of a medical procedure, a type of fluid or medication, a medical personnel, a medical condition and a combination of these.

A method for managing use of an IV set system having a primary IV set and at least one separably joined secondary IV sets can comprise initiating application of an IV to a patient along a primary IV set; identifying a first secondary IV set of the IV set system for administering a substance to the patient; at least partially stripping an upper end of the first secondary IV set from the IV set system to provide a free, unattached end to facilitate proper access and positioning thereof within the IV set system, while retaining an attached portion of the first secondary IV set, thereby reducing likelihood of entanglement of the primary and secondary IV sets; and stripping a lower end of the secondary IV set and coupling it to an access port located proximate a distal terminus of the primary IV set. The method can further comprise completely stripping the secondary IV set from the IV set system following use.

A method for bypassing a primary flow path of a primary flow line within a primary IV set can comprise obtaining a primary IV set having a plurality of access points facilitating access to one or more fluid pathways of the primary IV set, at least some of the access points comprising access ports providing fluid access to a primary flow line of the primary IV set; diverting fluid from the primary flow line to a bypass flow line of a manifold removably and externally coupled to the primary IV set via the access ports, the manifold comprising one or more access points that facilitate access to the bypass flow line; and providing, through the manifold, an alternate primary flow path to a primary flow path through the primary flow line. The method can further comprise selectively actuating a flow control valve operable to selectively occlude fluid flow through the primary flow line of the primary IV set and to divert the fluid through the manifold and the bypass flow line; restoring fluid flow through the primary flow line of the primary IV set.

Pre-Coded IV Sets/Set Systems

Some exemplary embodiments of the present invention represent a change in perspective, endeavoring to actually anticipate and preserve some measure of historical data regarding use of the IV set system as part of the IV structure itself. For example, a multi-set IV set system can be applied which is capable of being adapted for use in subsequent procedures without discarding earlier components and applications of the IV set system. Specifically, various routine IV procedures can be structurally encoded by incorporating a particular color, shape or appropriate identification to differentiate the various IV sets of the IV set system. These various IV sets can be selectively utilized at sequential stages of medical care of the patient. By making a quick inspection of the patient's IV set system, subsequent attending personnel can quickly identify those procedures having been applied to this patient under prior medical procedures simply by examining the IV set system and the various IV sets therein to see which IV sets were used, how they were used, if they were used, etc.

In some aspects, to avoid inappropriate repeated use of a given secondary IV set, that secondary IV set can be partially or completely stripped away from the primary IV set and discarded. Nevertheless, the identity of the discarded secondary IV set can be preserved at the primary IV set for future reference by configuring the IV sets, or their various access points, to comprise matching indicia. More specifically, the secondary IV set(s), and/or their access points, can comprise indicia that matches indicia the primary IV set. For example, the primary IV set can comprise an access port operable to fluid couple or interconnect with a corresponding access point on a secondary IV set. The access port of the primary IV set can comprise indicia that matches indicia on the access point of the secondary IV set. Therefore, in the event the secondary IV set is discarded, corresponding or matching indicia present on the remaining primary IV set can indicate the previous presence of the discarded secondary IV set, which indicia can provide useful historical data to medical personnel.

Providing pre-coded IV sets within the IV set system itself provides an initial cue to patient information, the details of which are provided on the patient chart. Providing pre-coded IV sets can also speed up the decision process by increasing the awareness of medical personnel with respect to the patient's treatment history. Of course, in order to minimize entanglement and confusion, some IV sets can be purposefully adapted to be quickly stripped from the IV set system or rendered unusable when their historical value is nominal.

The use of individually distinguishable IV sets having standard unique designations corresponding to standard IV procedures gives medical personnel the ability to quickly select an appropriate IV set from among the various available marked IV sets within the IV set system. For example, the use of a coded set specifically reserved for pain medication among the plurality of IV sets within the IV set system provides the medical attendant with an immediate preference of choice in selecting an IV set for administering pain medication.

Accordingly, the development of pre-coded IV sets as part of an IV set system provides at least two significant advantages. First, such a practice would assist medical staff in quickly identifying previous procedures applied to the patient, thereby increasing the level of awareness of medical personnel to the patient's history. In addition, having multiple pre-coded IV sets available could simplify the selection of an appropriate line for a current procedure. For example, with a knowledge of a specific, predetermined function of the IV set to be applied, attending personnel can quickly identify the corresponding set which has that coded function. Many forms of identification can be applied with respect to the individual sets of an IV set system. These may include, but are not limited to, specific colors, shapes, tactile indicators or indices, tags or other indices that could be respectively allocated and standardized for medications associated with blood, pain medication, anesthesia, etc., as well as any others and/or combinations of these.

Rather than having only a single IV set system tor universal application, it may be desirable to develop specific groups of IV set systems selected to correspond with particular medical conditions having foreseeable IV requirements, to correspond with particular personnel, or to correspond to particular procedures. Surgical patients, for example, could be treated with a single IV set system specifically configured for use by the anesthesia provider and other members of the surgical team. Other patients having unique conditions could have a unique IV set system specifically configured for procedures, such as an endoscopy, related to their specific conditions. By having IV set systems specifically configured or tailored to particular medical conditions, procedures or personnel, clarity and convenience are greatly enhanced.

IV Set/Access Point Identification

In current designs, primary IV sets contain multiple access points that facilitate access to one or more fluid pathways within the IV set. For example, IV sets comprise access points through which fluids (e.g., medications) may be administered. It is standard practice that when an IV is started on a patient that a carrier fluid (normal saline is one example) will be attached and administered. Future medications are administered through the access points along that primary IV set. These access points allow medications to be given over multifarious intervals (i.e. rapid administration of medications pushed through a syringe by a practitioner, additional IV sets added and medications given at a rate determined by the position of a roller clamp or more specifically by a pump with a set rate, etc.) As additional IV sets are used with this primary (carrier) IV set and the growing compilation of IV sets, the potential for miss-identification of access points belonging to the primary IV set increases exponentially. For example, if a primary IV set contains four access points, an additional or secondary IV set could also contain two, three, four or more access points. These additional access points may be difficult to distinguish from those of the primary IV set.

Confusion as to the correct identity of a given IV set within a compilation of IV sets can be a serious life threatening risk to the patient and great frustration to attending medical personnel. In almost all medical situations involving the use of multiple IV sets with a single patient, even the most vigilant practitioners must take valuable time to differentiate the primary/carrier IV set from other medication IV sets. This difficulty is intensified in emergency and other high stress situations and environments where mistakes can be magnified or the number of mistakes increased as decisions often need to be made immediately. With the possibility of potent medications being delivered through secondary IV sets, an inadvertent bolus from a drug being pushed through these secondary medication IV sets could be lethal. In addition, there is the constant danger of mixing incompatible medications or fluids. It is necessary, therefore, to be constantly concerned with which access points go with which IV sets. The general absence of standardized labels and standardized positioning of these labels along the IV sets, as well as inadequate IV access point identification, presents an ongoing medical risk.

One exemplary embodiment of the present invention includes the addition of marking indicia on or about (in close proximity to) at least two access points, and alternatively at or about each access point, of the primary IV set. Such marking indicia can further be located on or at other locations along the primary IV set. The marking indicia function to help locate and differentiate the primary IV set and its access points from other secondary IV sets either initially present, or added throughout the healthcare delivery process. Accordingly, the primary IV set itself and/or the various access points along the primary IV set can be configured with unique and marking indicia to distinguish it and the access points from other secondary IV sets to facilitate rapid line identification. Furthermore, both the proximal and distal termini, and/or the various access points, of each secondary IV set can also have unique marking indicia different from the primary IV set and other secondary IV sets to distinguish them for rapid identification of priming, connection and disconnection.

Figure 2A:
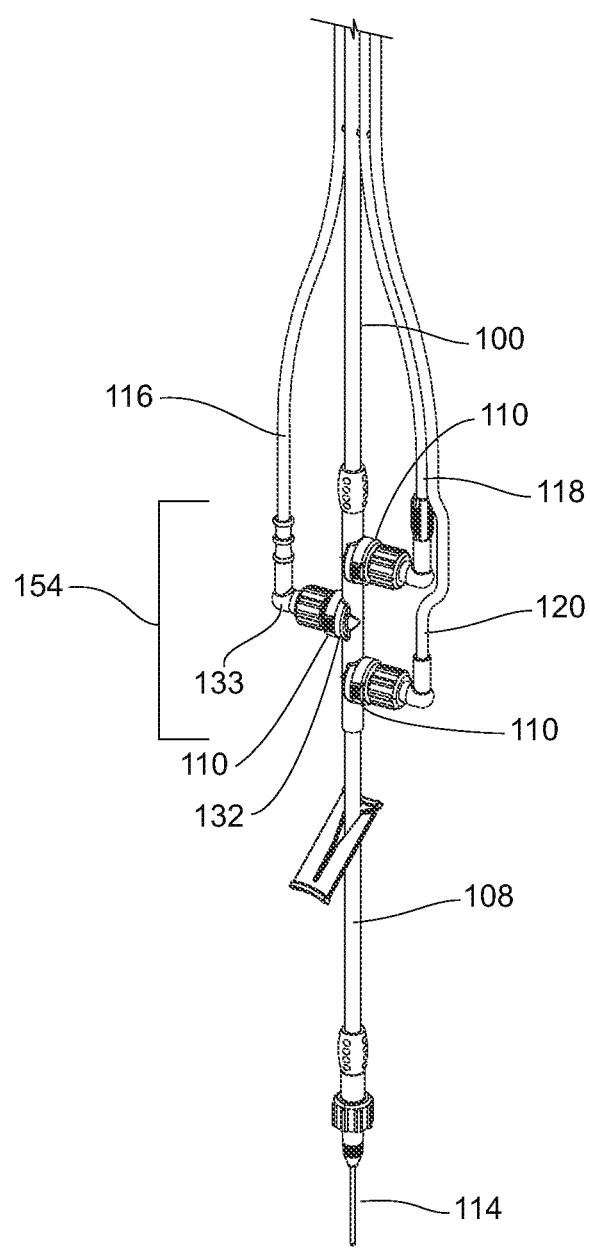
FIG. 2A illustrates a partial plan view of the exemplary IV set system of FIG. 1, and particularly one exemplary embodiment of a merging fluid pathway for the IV set system.
Figure 2B:
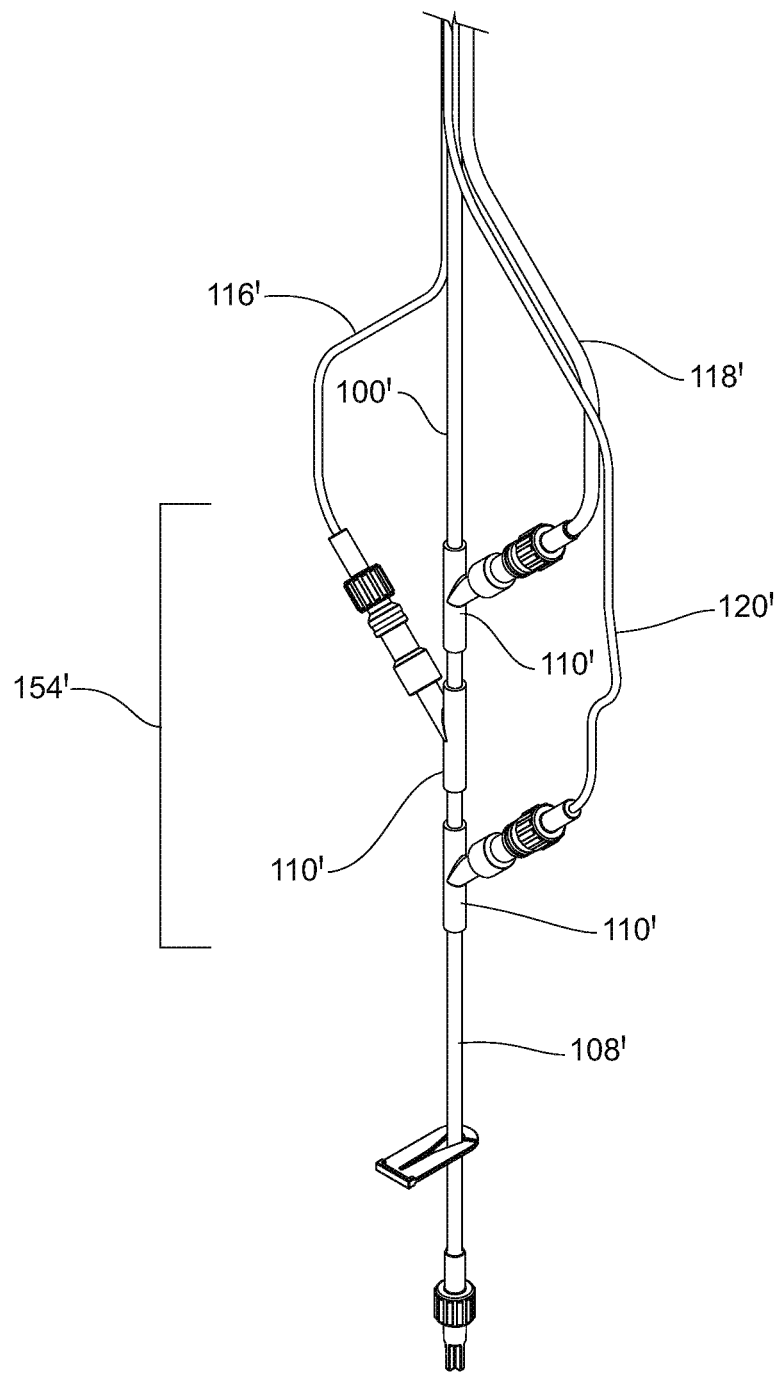
FIG. 2B illustrates a partial plan view of the exemplary IV set system of FIG. 1, with an alternative merging fluid pathway and access port configuration.

Specific exemplary methods and features of line identification can include the techniques and structures shown in FIGS. 1-2B. Specifically, an IV set system in accordance with an exemplary embodiment of the present invention can include a primary IV set 100 having a proximal terminus 102, a distal terminus 104, and an intermediate tubular length 106 defining a primary flow line 108 of the primary IV set 100, such as for providing saline carrier fluid. The primary flow line 108 can have multiple access ports 110 along its length, such as for administering various medications needed by the patient, facilitating coupling of an external manifold to establish a bypass flow line, and others. These access ports 110 can be self-sealing, meaning that they are capable of facilitating flow when in use, and prohibiting or sealing off flow when not in use. The access ports 110 can comprise any type or can be used for any purpose as recognized by those skilled in the art. For example, the access ports 110 can be used to couple or removably couple a syringe for pushing fluid into the primary flow line 108, they can be used to couple or removably couple a secondary IV set to facilitate infusion of a fluid into the primary flow line 108, etc. In one example, the access ports 110 can comprise a first connector portion of an interconnect or connector operable to couple with a second connector portion of the interconnect or connector.

In the example shown, the access ports 110 each comprise a first connector portion 132 in the form of a female portion of a Luer Lock. The secondary IV sets each comprise a second connector portion 133 in the form of a male portion of a. Luer Lock.

The IV set system can further comprise at least one secondary IV set e.g., see secondary IV sets 116, 118, 120) physically and removably coupled to the primary IV set 100, such as via access ports 110. The one or more secondary IV sets 116, 118 and 120 can further be removably and fluidly coupled to the primary IV set 100 via the one or more access ports 110 of the primary IV set 100, such as via those forming the merging fluid pathway 154, wherein the fluid flow paths of the secondary IV sets 116, 118 and 120 and the primary IV set 100 are in fluid communication with one another, or in other words, conic together or merge.

The IV set system can further comprise a merging fluid pathway 154 comprised of at least one access port 110 on the primary IV set 100. The merging fluid pathway 154 can be positioned on the primary IV set 100 about the primary flow line 108 proximate to the distal terminus 104 to minimize the amount of fluid in the primary IV set between the merging fluid pathway and the patient interconnect. The access ports 110 of the merging fluid pathway 154 can be spaced at a predetermined distance from each other about the primary IV set 100. In the example shown in FIG. 2A, the access ports 110 can be oriented at a 90-degree orientation relative to the primary flow line 108. As one skilled in the art will recognize, other angular orientations may be used where merited by the circumstances, such as angular orientations between 30 and 150 degrees (as measured from the longitudinal axis of the primary line 500), or even others. For example, FIG. 2B illustrates that the IV set system of FIGS. 1 and 2A can comprise an alternative configuration of a merging fluid pathway. In this example, the merging fluid pathway 154' comprises access ports 110' oriented on about a 30 degree orientation relative to the primary flow line 108' of the primary IV set 100'. This orientation will likely provide smoother flow transitions of fluids from the secondary IV sets 116', 118', and 120', shown as being fluidly coupled to the primary IV set 100', into the flow path of the primary IV set 100' over the configuration of the access ports 110 shown in FIGS. 1 and 2A oriented on a 90 degree orientation.

In one example, the one or more secondary IV sets 116, 118 and 120 can by physically and separably connected to the primary IV set and/or one another. As such, the secondary IV sets 116, 118 and 120 can be configured to be stripped or peeled away from the primary IV set 100 as needed as desired. This concept is discussed in greater detail below. Each secondary IV set can comprise a proximal terminus 122, a distal terminus 124, and an intermediate tubular length 126.

Current methods and materials for fluidly interconnecting IV sets and couplings are well known and are not further described, except where modifications are particularly noted as part of the invention. For example, the proximal termini of the primary IV set 100 and the one or more secondary lines can be adapted with a coupling structure 130 for receiving a fluid source to be coupled to the IV set for providing at least one fluid medium to a patient through the primary IV set 100. Similarly, the distal terminus 124 of the one or more secondary line(s) can include fluid interconnect means 132 for attaching the distal terminus 124 of the one or more secondary lines to one of the access ports 110 of the merging fluid pathway 154 near the distal terminus 104 of the primary IV set 100. Finally, the distal terminus 104 of the primary IV set 100 can further include a patient interconnect structure 134 for coupling the primary flow 108 of the IV set to a patient injection site 114.

The merging fluid pathway 154 can comprise at least one access port/fluid interconnect in direct fluid communication with the primary flow line 108 of the primary IV set 100. The merging fluid pathway 154 can be located anywhere along the primary IV set 100. In one aspect, the merging fluid pathway 154 can be located on the primary IV set 100 below a midpoint of the primary IV set 100. In another aspect, the merging fluid pathway 154 can be located on the primary IV set 100 at or near the distal terminus 104 of the primary IV set 100. In a more specific aspect, the merging fluid pathway 154 can comprise the distal most access ports/fluid interconnects of the primary IV set 100, such as those access ports 110 shown in FIG. 2A. These can be configured to couple with the distal termini of the one or more secondary IV sets (e.g., IV sets 116, 118 and 120 of FIG. 2a) to facilitate fluid flow from the one or more secondary IV sets directly into the fluid pathway in the primary IV set 100. Generally speaking, the merging fluid pathway 154 can provide a merging of fluid from the fluid source (e.g., secondary IV set, syringe, etc.) connected to it directly with the fluid of the primary IN set 100.

In one example, being located at or near the distal terminus 104 of the primary IV set 100, the merging fluid pathway 154 can provide a final stage of fluid injection or infusion to the primary flow line 108 of the primary IV set 100 prior to the point of attachment of the primary IV set 100 to the patient at injection site 114. This final stage may also be followed by a final segment of flow along the distal terminus 104 of the primary IV set 100 to facilitate the merging of fluids within the primary flow line 108 immediately prior to injection into the patient. This is likely an ideal position for coupling one or more secondary IV sets (e.g., secondary IV sets 116, 118, 120) and fluidly connecting their respective flow lines because it allows merging of other fluids and medications into the primary flow line 108 proximate to the patient injection site 114. The location of the merging fluid pathway 154 proximate to the patient injection site 114 has many benefits, as taught herein, and as will be recognized by those skilled in the art. For example, and not intending to be limiting in any way, these benefits can include precise timing of medications, rapid drug response due to location just proximate to IV insertion site, thus avoiding delays in delivery of medication to the patient, strict control of fluid volume, the ability to disconnect secondary lines leaving minimal amount of medication in the primary line, and the ability to disconnect and reconnect to the merging fluid pathway 154 during a patients multi-staged care. In addition, this configuration provides increased hemodynamic stability independent of change to the rate of flow through the primary flow line 108. This merging fluid pathway 154 may be arranged in a unilateral orientation (extending in the same direction within a common plane), bilateral (extending in opposing directions) (e.g., see FIG. 2) or circumferential arrangement (extending radially outward). The placement of this merging fluid pathway 154 can provide the caregiver with many options for both fluid management and medication delivery control.

In other embodiments, each of the proximal terminus, access points, and distal terminus of the primary IV set 100 can include one or more unique marking indicia to distinguish the primary IV set 100 (an its access points) from one or more secondary IV sets, and to facilitate rapid line identification for each IV set within the IV set system. The marking indicia can be uniform, or configured in accordance with some other arrangement. Any slide clamps, roller clamps, or other elements associated with the primary IV set 100 can comprise the same indicia as the other indicia on the primary IV set 100. Similarly, the respective proximal terminus, access points, and distal terminus of arty or all secondary IV sets can include one or more unique marking indicia to distinguish it from other secondary IV sets and the primary IV set that may have differing indicia. These too can be uniform or configured in accordance with some other arrangement. Still further, the primary IV set 100 can comprise both top-level and second-level marking indicia, wherein the second-level marking indicia matches the marking indicia on a secondary IV set operable with the primary IV set 100. These concepts are explained in more detail below with respect to other embodiments, although applicable and contemplated for use with the IV set system of FIGS. 1-2B. In other words, the present description pertaining to coding of the various IV sets within an IV set system is applicable to the IV set system of FIGS. 1-2B, even if such description is in relation to another embodiment. Essentially, the IV set system illustrated in FIGS. 1-2B cart comprise marking indicia as set forth and described in any of the embodiments discussed herein, as will be recognized and as can be applied by one of ordinary skill in the art.

The IV set system of FIGS. 1-2B can further comprise individual IV sets (primary and one or more secondary IV sets) that are physically and separably joined together in at least a semi-continuous manner substantially along their length, such as by attachment members 160, to inhibit entanglement with one another, in some aspects, the IV sets separably joined together in a manner that facilitates partial or full stripping of one IV set from another IV set. It is contemplated herein that the IV set system of FIGS. 1-2B can comprise separably joined IV sets as set forth and described in any of the embodiments discussed herein, as will be recognized and as can be applied by one of ordinary skill in the art.

Figure 3A:
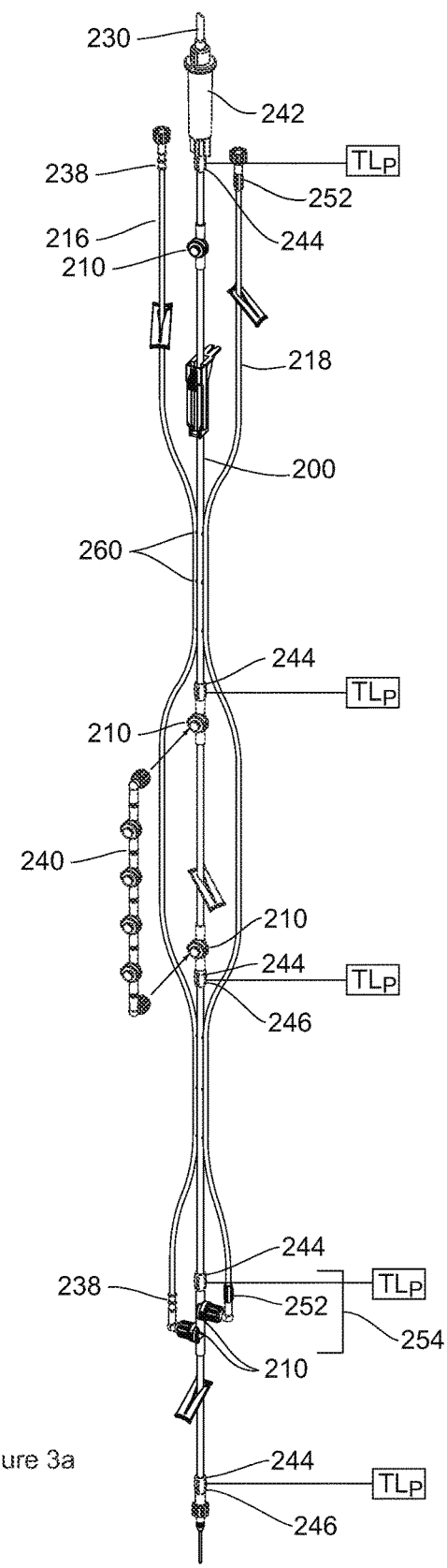
FIG. 3A illustrates a plan view of an IV set system in accordance with another exemplary embodiment of the present invention, the IV set system having several example embodiments of marking indicia.

The IV set system of FIGS. 1-2B can further comprise a manifold 140 externally coupled to the primary IV set via at least some of the access ports of the primary IV set, the manifold comprising a bypass flow line adjacent the primary flow line, and one or more access points that facilitate access to the bypass flow line, wherein the manifold and the bypass flow line provide an alternate primary flow path to a primary flow path through the primary flow line. It is contemplated herein that the IV set system of FIGS. 1-2B can comprise a bypass manifold as set forth and described in any of the embodiments discussed herein, as will be recognized and as can be applied by one of ordinary skill in the art, FIG. 3A illustrates an IV set system in accordance with another example of the present disclosure. The IV set system in FIG. 3A is similar in many respects to the IV set system illustrated in FIGS. 1-2B in that it can comprise many of the same elements. As such, the discussion above with respect to the example IV set system of FIGS. 1-2B is applicable to the IV set system of FIG. 3A unless otherwise noted. Like the IV set system in FIGS. 1-2B, the IV set system in FIG. 3A comprises a plurality of secondary IV sets attached to a primary IV set 200. The IV set system of FIG. 3A can further comprise a merging fluid pathway 254 as set forth and described in any of the embodiments discussed herein, as will be recognized and as can be applied by one of ordinary skill in the art. The IV set system of FIG. 3A can further comprise a bypass manifold 240 as set forth and described in any of the embodiments discussed herein, as will be recognized and as can be applied by one of ordinary skill in the art.

With respect to the concept of marking indicia, in the example shown, the secondary IV set 216 is shown as being distinguishable from the other secondary IV set and the primary IV set 200 by clearly marked indicia, namely circular rings 238, located at both the proximal and distal termini or the secondary IV set 216. In one aspect, the primary IV set 200 can comprise its own, different marking indicia, as discussed above. For example, along the primary IV set 200 the spike structure 230 above the drip chamber 242, as well as the various access ports 210, can have a different set of marking indicia that distinguishes the primary IV set 200 from any of the secondary IV sets.

In one embodiment, these marking indicia can form part of the original construction of the respective lines of the IV set, being fabricated as part of the original structure. These marking indicia may include, but are not limited to texture, color and shape. Alternatively, the marking indicia can be manufactured independent of the IV sets, and later applied or otherwise associated with the various primary and secondary IV sets of the IV set system subsequent to their initial manufacture. There are a variety of ways and means by which the marking indicia can be associated with the lines in the IV set system, as will be recognized by those skilled in the art. For example, the marking indicia can comprise various objects, indicators, etc. that can be applied or otherwise associated with the various lines of the IV set system using adhesives, clamps, snap-on systems, fasteners, etc. Such marking indicia may also include color, geometric shape, size and texture, or any other tactile and/or visual element that can enable the attending personnel to quickly and accurately identify a given IV set within the IV set system.

Figure 3B:
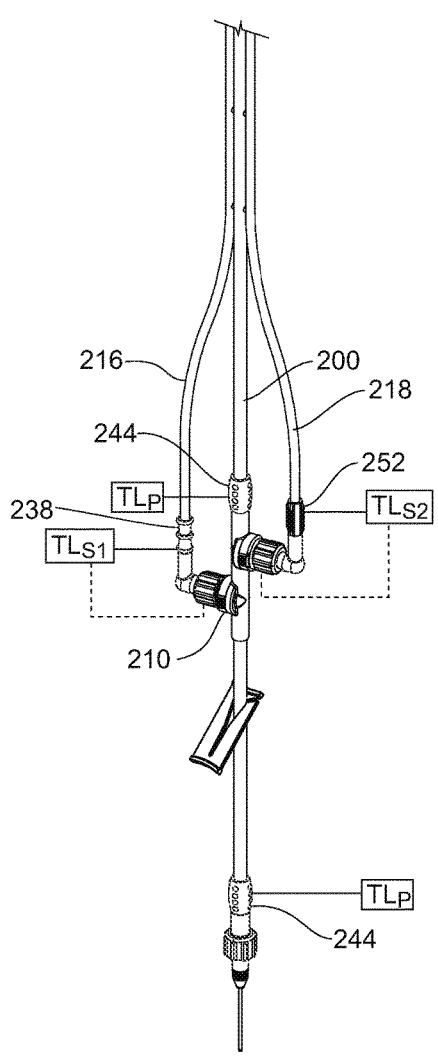
FIG. 3B illustrates a partial plan view of the IV set system of FIG. 3A.
Figure 3C:
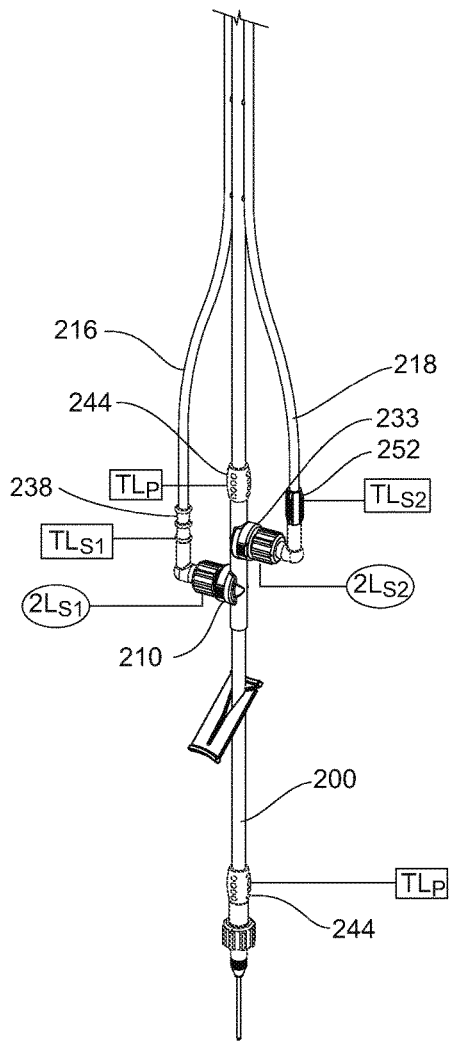
FIG. 3C illustrates a partial plan view of the IV set system of FIG. 3A.
Figure 3D:
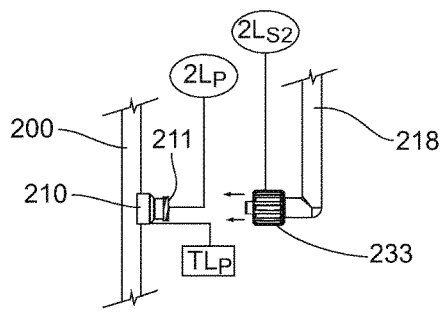
FIG. 3D illustrates a partial side view of the IV set system of FIG. 3A.

With reference to FIGS. 3A-3B, each of the IV sets, including spikes, drip chambers, access ports, proximal and distal termini, clamps, etc., can comprise top-level indicia, identified as top-level indicia "TL," specific to that particular IV set, yet different from the top-level indicia of surrounding IV sets. In other words, each IV set in the IV set system can comprise a different set of top-level indicia, which can be uniform (the same), wherein their primary function is to identify and distinguish each IV set from any other IV set in the IV set system. 10 the example shown, the primary IV set 200 comprises top-level indicia $TL_P$ at the proximal and distal termini. Furthermore, the primary line 200 comprises top-level indicia $TL_P$ along its length. The top-level indicia can be uniform about the length of the primary IV set 200. Specifically, the primary IV set 200 comprises top-level indicia $TL_P$ in the form of a plurality of spherical shaped objects 244 located at the proximal and distal termini, as well as at or near the drip chamber 242, and access ports 210. The spherical objects 244 can further comprise additional indicia, such as a textured surface (see pattern of bumps 246 formed thereon). Numerous variations in colors, shapes and textures can be employed. Alternatively, the primary IV set 200 can comprise top-level indicia located directly on each of its access points, such as the access ports 210 (e.g., the access ports 210 comprising a distinguishing color).

The secondary IV sets 216 and 218 physically and fluidly coupled to the primary IV set 200 can also comprise top-level indicia "$TL_{S1}$" and "$TL_{S2}$," respectively, which can be uniform about the length of the secondary IV sets 216 and 218. Specifically, in the example shown, secondary IV set 216 comprises top-level indicia $TL_{S1}$ in the form of circular rings located at the distal termini, and secondary IV set 218 comprises top-level indicia $TL_{S2}$ in the form of colored adhesive strips 252. Secondary IV sets 216 and 218 can alternatively comprise top-level indicia directly on each of its access points, such as the interconnects on the proximal and distal termini. In another example, and although the drawings illustrate the secondary IV sets 216, 218 as comprising indicia, it is contemplated that the secondary IV sets 216, 218 can be devoid of indicia, wherein if used with the primary IV set 200 these two IV sets will be distinguishable from one another.

With reference to FIGS. 3A-3D, each of the primary and secondary IV sets within the IV set system can each further comprise one or more second-level marking indicia, wherein the second-level marking indicia from one IV set can be configured to match with a corresponding second-level indicia of another IV set, thus providing a set of matching indicia across IV sets. In one example, the matching indicia can operate to provide a particular identifying trait or feature pertaining to the associated IV sets. In the example shown, the primary IV set 200 comprises second-level indicia "$2L_P$" located on a nipple 211 of an access port 210 operable to fluidly and removably couple with an interconnect portion 233 located on the distal termini of the secondary IV set 218, thus the matching second-level marking indicia is intended to be located on or about or in close proximity to two access points of the primary and secondary IV sets that correspond with or that are intended to correspond with one another (e.g., the fluid coupling of an access point on the secondary IV set with a particular access port on the primary IV set). Likewise, the secondary IV set 218 is shown as comprising second-level indicia "$2L_{S2}$" on the interconnect 233 that couples to the access port 210. The second-level indicia of the primary IV set 200 can be configured to match the second-level indicia of the secondary IV set 218 at the location where the secondary IV set 218 couples to the primary IV set 200. For example, the second-level indicia $2L_P$ and $2L_{S2}$ can be colored coded to comprise the same color. In this example, with the secondary IV set 218 coupled to the primary IV set 200, the second-level indicia of the primary IV set 200 is concealed, thus maintaining the uniformity of indicia about the primary IV set 200 by way of the top-level indicia thereon. However, in those situations where the secondary IV set 218 is not coupled to the primary IV set 200, or removed therefrom, the second-level indicia of the primary IV set 200 will be visible to attending medical personnel. With the second-level indicia $2L_P$ on the primary IV set 200 visible, medical personnel can quickly and easily perform line identification and other tasks, as well as possibly being provided with historical data pertaining to the use of the IV set system. Matching indicia present on the remaining primary line can indicate the previous presence of the particular secondary IV set 218. Those skilled in the art will recognize that the second-level indicia $2L_{S2}$ on the secondary IV set 218 can function as a top-level indicia. In this case, it is contemplated that the secondary IV set 218 will only comprise only a single level of marking indicia, namely indicia that matches the second-level indicia on the primary IV set 200. Those skilled in the art will also recognize that secondary IV set 216 operable with the primary IV set 200 can also comprise its own top-level and/or second-level indicia different from that of the first secondary IV set, and that matches different second-level indicia on the primary IV set 200, such as that associated with another access port 210.

The use of multiple or different indicia (e.g., including one or more of shape, size, color and texture) will enhance the sure identification of the various IV sets. Furthermore, by standardizing specific indicia for common IV applications (e.g., standardizing indicia types), experience and common usage will further enable rapid identification. For example the following general IV applications might be associated with the following marking indicia types:

a. Vasopressors—indicia type one (e.g., purple)
    b. Paralytics—indicia type two (e.g., red)
    c. Narcotics—indicia type three (e.g., blue)

The marking indicia can be further coordinated to represent a group of medical IV procedures corresponding to a particular medical condition or procedure. In this manner, medical specialists can become accustomed to the regular and exclusive use of particular indicia associated with their field of medicine. Such examples can include:

a. Chemotherapy—colored strips or other annular indicia. See colored adhesive strips 252).
    b. Endoscopy—bumps In this manner, progressive advancement of each patient type through a given set of procedures can be historically recorded within the IV set system of the patient. Attending medical personnel can also be assisted in making a correct selection of an IV set in any given procedure based on the IV code identification, rather than merely making random selection of a line from a bundled IV set. An overall advantage of such a system can be to contribute to improved organization and access to the respective IV sets, as well as improved predictability in the administration of an IV. It will be apparent to those skilled in the art that the concepts of unique identification set forth in this application can be modified in various ways without departing from the invention.

Strippable IV Sets as Part of a Separably Attached IV Set System

IV line entanglement is also a major concern in any tertiary care facility. Not only is safety a concern, but time and ease of management for practitioners in these environments is also a worry. As an example of benefits associated with the present invention utilizing, for example, color or other indicia coded components, consider a typical experience of a 70 year-old patient arriving at the emergency department with a fracture of the femur. On being admitted, it is determined surgery will be necessary. Suppose the patient has a history of hypertension, coronary artery disease and is a non-insulin dependent diabetic. Knowing this, an appropriate IV set system having physically removably coupled and integrated multiple flow lines having various marking indicia thereon can be selected for the patient. Using a multi-set system with indicia coded lines for the respective potential medications and fluids for this patient provides familiar IV set system choices for each attending medical person. The present disclosure contemplates and the described invention facilitates use of a single IV set system for the length of the stay and across multiple stages of care.

The selection process can include an awareness of the patient's existing co-morbidities. In this hypothetical situation, a three-set (e.g., one primary and two secondary IV sets) within the IV set system can be utilized for IV management. The main or primary IV set can be used for IV fluids and to push medication administration to the patient injection site. The two secondary IV sets can be available for IV drip or medication infusions as needed. The patient can then be prepped for the operating room using this single IV set system.

Upon arrival at the operating room the anesthesia provider can quickly visually inspect and interrogate the IV set system and its coded IV sets and corresponding flow lines and identify or determine which line is to be used for administering general anesthesia. In the event at some point the patient becomes hypotensive and a vasoactive medication drip needs to be administered through one of the secondary IV sets, one of these components of the IV set system can also already be available for use and easily identifiable with its distinguishable marking indicia. An insulin drip can be on standby and ready for use to be administered through the remaining secondary IV set if needed. Furthermore, in the event the patient stays overnight in the surgical ward, and when the patient stabilizes, it is likely that the insulin and vasoactive medications will no longer be needed. As such, before leaving the operating room, the anesthesia provider can stop the additional infusions and strip away or remove one or more of the two secondary IV sets from the other secondary IV sets and/or the primary IV set, which can remain intact for use on the surgical ward. As can be seen, the use of coded IV sets can avoid the prior known difficulties of selection in the various medical situations encountered.

Simplifying the process of IV set selection and maintenance, allows the medical staff to avoid unnecessary intermingling of the various IV sets within the IV set system that might otherwise lead to entanglement. Because the different IV sets are color coded (or otherwise uniquely marked and identifiable), such as at the proximal and distal termini, and/or at or near access points along the intermediate sections, IV sets are more easily managed during use. Marking each IV set enables personnel to quickly and easily identify the various flow lines of the IV set system, maintain separate alignment of these IV sets, and avoid weaving and entangling the various lines amongst each other, thus easing use of IV sets during medical situations, particularly during emergency and other stressful situations. Otherwise, without clear identification, a user might grasp what he/she believes is the correct line, subsequently realize the error, and quickly attempt to take another line and reposition it where needed. Eventually, these lines may become interwoven, further complicating the correct identification.

One can also see that at each successive stage of a hospital stay, it is possible that medical staff personnel can change, with newly attending personal becoming involved with management of a patient's IV set system. When multiple medical personnel are involved, particularly when each person is dealing with different medical issues, the combinations of procedures involving the IV set system become even more complex. If the patient from the above example experiences complications leading to transfer to the intensive care unit, multiple IV sets may become attached to one or more IV catheters inserted into the patient. If current IV set types are added, these being without clear identification means, and without inter-attachment of lines in an orderly manner, no means of controlling and physically organizing these IV sets would exist, leading to a confusing mass of fluid pathways often referred to as a "spaghetti pile". If surgery is again needed, any additional current IV set types added to the patient's compilation of IV sets would increase the entanglement problem. However, with the present IV set system the use of marking indicia (e.g., standardized marking indicia) on each IV set, and integrally coupled IV sets (see FIGS. 5 and 6), such confusing situations of line entanglement can be easily avoided.

The present invention can minimize problems of line entanglement by allowing IV sets to be physically joined or coupled together in a removable manner. For example, each IV set system can comprise a primary IV set and one or more secondary IV sets joined to the primary IV set and/or an additional secondary IV set. Additionally, each line of each IV set can be properly coded for unique identification. Secondary IV sets can further be appropriately fluidly coupled to the primary IV set, providing a recognizable system for the attending personnel. As is explained hereafter, a manifold coupling system can also be used with the IV set system to simplify multiple stages of patient treatment. If medical staff members are uncertain of the potential procedures to be applied to a patient, an IV set system can be selected which includes physically and separably joined or connected (e.g., integrally separably connected) IV sets for several likely procedures that could arise, enabling attending individuals to have immediate access to an existing IV set coupled to the patient. The versatility of pre-coded IV sets grouped for pre-selection according to the anticipated needs of the patient offers greater convenience, safety, and ultimate cost savings over prior IV set solutions through reduction of errors and risks within the medical care arena.

As can be noted from the previous example, this invention is well suited for use in common or other medical situations or practices calling for an IV set up. The following four examples illustrate this concept, and are not intended to be limiting in any way, Example 1

TIVA

A Total Intravenous Anesthetic or TIVA is the administration of anesthesia utilizing IV medications as opposed to inhaled anesthetics to maintain a general anesthetic. Common medications essential, but not limited, to a TIVA are a hypnotic/sedative agent and narcotic agent.

Merging Fluid Pathway

The present IV set system is designed to facilitate and enhance this anesthesia approach. In some example configurations, the merging fluid pathway (MFP) can be located on the primary IV set at or near the distal terminus. As indicated above, the MFP can comprise at least one access port/fluid interconnect on the primary flow line in close proximity to the distal terminus of one or more secondary IV set(s) to subsequently be fluidly coupled to the primary IV set. These secondary IV sets can be physically and separably joined (e.g., integrally secured) to the primary IV set in a parallel relationship in at least a semi-continuous manner at least partially along their tubular length to inhibit line entanglement, facilitate rapid line identification and gravity priming (see, for example, the representative methods of attachment between the primary and secondary IV sets illustrated in FIGS. 5 and 6). Attachment between IV sets maintains the respective lines in an orderly array, even when several attending personnel are concurrently making use of the IV system for various procedures. Coding indicators on one or more of these lines enables rapid identification in accordance with the intended purpose for any given line and/or access port. The location of both the distal terminus of the secondary line(s) and location of the merging fluid passageway are ideal as they provide the caregiver with both a secondary medication line and an access point in close proximity to one another, wherein the secondary IV set can conveniently be fluidly coupled to an access port of the merging fluid passageway. To summarize, some of the advantages of an IV system incorporating a merging fluid pathway as disclosed include the following:

1. The ability to administer medications at a distal location while maintaining hemodynamic stability regardless of flow rate changes in the primary flow line;
2. The ability to discontinue one or more secondary lines with minimal residual amounts of medication in the primary flow line, thereby decreasing the risk of an over dose; and
3. Allowance for rapid onset of any secondary medication(s) administered through a secondary line due to the distal location of the MIP; even with slow primary flow rates.

Example 2

Endoscopic Procedures

During endoscopic procedures, anesthetic agents are often used to facilitate scope and instrument placement and manipulation as well as patient comfort. A sedative/hypnotic agent infused, using an IV pump via a secondary IV line, into the primary IV line is often used as the primary means of anesthesia. The present IV set system will allow a secondary IV set that is separably joined to a primary IV set as the means of administrating the sedative/hypnotic agent. Advantages are reduced line entanglement and allowance for rapid onset of any secondary medication(s) administered through a secondary IV set due to the distal location of the MFP; even with slow primary flow rates, Example 3

Complex Patient

Anesthesia for a complex patient involves administration of many different medications, often simultaneously, and includes but is not limited to sedatives/hypnotics, narcotics, paralytics, insulin, vasopressors to manipulate blood pressure, and medications to support heart rate, and contractility of the heart. IV access is often limited so all these medications are run via secondary IV sets connected to syringe and infusion pumps into a primary IV set that serves to deliver the carrier fluid. Over fluidization, line entanglement and IV set identification are constant problems encountered during these complex cases, With the limited number of access ports on currently available primary line IV sets, distal connection for these potent and potentially lethal medication lines is an issue. Some embodiments of the present IV set system solve these problems and provide various advantages, such as allowance for rapid onset of any secondary medication(s) administered through a secondary line due to the distal location of the MFP (even with slow primary flow rates), thus reducing total fluid required through the primary IV set limiting over fluidization; reduced line entanglement and identification difficulty related to all secondary IV sets being separably connected to the primary IV set and having each with its own unique marking indicia to allow for rapid identification of each separate line; the ability to administer medications at a distal location while maintaining hemodynamic stability regardless of flow rate changes in the primary flow line; the ability to discontinue one or more secondary IV sets with minimal residual amounts of medication in the primary flow line, thereby decreasing the risk of an over dose; and others as will be recognized by those skilled in the art. In accordance with the present invention, the array of a plurality of secondary IV sets integrally connected in combination with a primary IV set avoids the inevitable entanglement of the various lines during patient care. IV set positioning remains orderly and predicable throughout the applied procedures by numerous medical personnel. Rapid identification of each IV set with its designated function is facilitated by appropriate marking indicia provided on the IV sets.

As indicated above, the present invention provides for separable attachment at least between the secondary IV sets of the IV set system, and also with the primary IV set as well. To further assist the medical staff to avoid the entanglement problems, as well as aid in correct and prompt identification of an appropriate IV set, the present invention incorporates the ability to fully or partially strip one or more separably connected IV sets away from the other IV sets when they are no longer needed or no longer serve a function. As such, it can be said that the IV set system, in some examples, can comprise one or more IV sets (primary, secondary, or both) that are separably connected to one another so as to be fully or partially separable or strippable. This property of "strippability" may be accomplished in several ways and with several types of construction. FIG. 3A illustrates the IV set system as comprising attachment points 260 that physically separably join the primary IV set 200 to the secondary IV sets 216 and 218. The IV set system illustrated in FIG. 3A can comprise separably joined IV sets as set forth and described in any of the embodiments discussed herein, as will be recognized and as can be applied by one of ordinary skill in the art.

Different embodiments illustrating separably joined IV sets and the associated strippable function are shown in FIGS. 4a and 4b. FIG. 4b illustrates an IV set system similar to the one shown in FIG. 3. The IV set system of FIG. 4b is shown as comprising a primary IV set 400 and two secondary IV sets 416 and 418 that are separably and physically joined together. In this particular example, the IV set system comprises a discontinuous type of attachment of the primary IV set 400 and the secondary lines 416 and 418 at fused locations 460 along the respective tubular flow line structures. In other words, discontinuous, isolated attachment members at fused locations 460 function to physically join the IV sets together. These attachment members at the various locations 460 are considered to be discontinuous as they are separated by unconnected segments of the tubular flow line structures. The isolated points of attachment or fused locations 460 cart comprise material integrally formed from the same material as the IV lines, or they can comprise a different material. In any event, the attachment members at fused locations 460 can comprise material that can facilitate the joining of one or more IV sets, and the selective separation or peeling away of these. In one aspect, the attachment members can be designed and configured to tear or rip. In another aspect, the attachment members can be designed and configured to separate or pull away from at least one of the IV sets.

Alternatively, FIG. 4a illustrates an IV set system comprising a primary IV set 300 and two secondary IV sets 316 and 318 having a continuous attachment member 362 between the primary IV set 300 and the secondary IV sets 316 and 318 that functions to separably join these together. In this example, the attachment member 362 can be comprised of the same material as the primary or secondary lines, and thus be integrally formed, or it can comprise a different material. The attachment member 362 can be disposed between one or more joined IV sets in a continuous manner, meaning that the IV sets are joined together without disconnected or disjoined segments within the attachment member 362. This does not necessarily mean that the IV sets are joined together along their entire length, although they could be. As such, the primary IV set and/or the secondary IV set(s) may be attached in a continuous manner along at least a portion of their length. Moreover, the attachment member 362 can be designed and configured easily tear or rip, or alternatively pull away from one of the lines.

One skilled in the art will recognize other systems, means, devices or methods in which the various lines in the IV set can be separably connected to one or more other lines in the IV set so as to facilitate the strippable functionality as described herein.

Stripping the IV sets from one another can occur as needed or desired, such as when a coded IV set is no longer needed or has already been used and therefore has no value (such as for historical purposes, for administering medication, etc.). Under these types of circumstance, the presence of any unnecessary IV sets can become a nuisance, interfering with access to still needed or required IV sets, as well as adding unnecessary IV sets that must be distinguished from those still needed by the patient. By stripping away these unnecessary IV sets, the bundle of IV sets within the IV set system is reduced, thus making the IV set system more manageable.

Figure 5A:
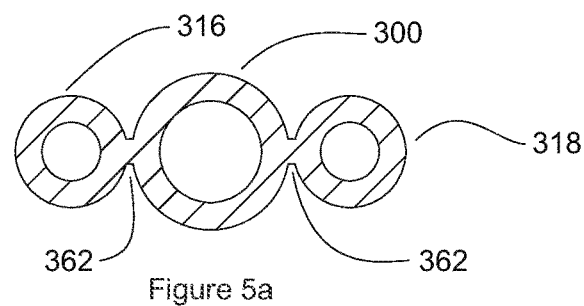
FIGS. 5a and 5b illustrate respective cross-sections of the exemplary IV set systems of FIGS. 4a and 4b.

More specifically, and with reference to FIGS. 4a and 5a, the exemplary primary IV set 300 and secondary IV sets 316 and 318 can be attached in an integral and continuous manner along all or a portion of their lengths. In this example, the IV set system can comprise a material portion or attachment member 362 disposed between the IV sets. In one example, the material portion 362 can comprise an extension of the same material as that used to form the tubular structures making up the IV sets. Stated differently, the tubular structures of the joined IV sets can be joined during their formation or manufacture. The tubular structures can be configured to comprise an outer wall portion and an inner wall portion that defines the interior bore or lumen of the tubular stricture. The tubular structures can further be configured to comprise an extension portion extending from the outer walls between them, the extension portion making up the attachment member 362. The attachment member 362 can be configured to space the tubular structures of the joined IV sets a given distance apart from one another. Furthermore, the attachment member 362 can be configured to comprise a suitable configuration (e.g., thickness, etc.) that will both maintain a properly joined arrangement during use of the TV set system, while also facilitating selective strip-ability as needed or desired. A continuous joining arrangement will allow the user to precisely control the amount of line to be stripped away.

Generally, as shown in FIGS. 4a and 5a, the at least one secondary IV sets 316, 318 can be secured to the primary IV set 300 in a parallel relationship, each secondary IV set having a proximal terminus; a distal terminus, and an intermediate tubular length secured via the attachment member 362 to the primary IV set in a continuous manner substantially along the intermediate tubular length to inhibit line entanglement within the IV set system. This secured attachment along the tubular length is configured in a manner so as to facilitate the peeling away of one or more secondary IV sets 316, 318 from the primary IV set 300 to provide variable free lengths of the proximal secondary IV sets 316, 318 as needed, such as for establishing secondary flow lines to the primary IV set 300.

Figure 5B:
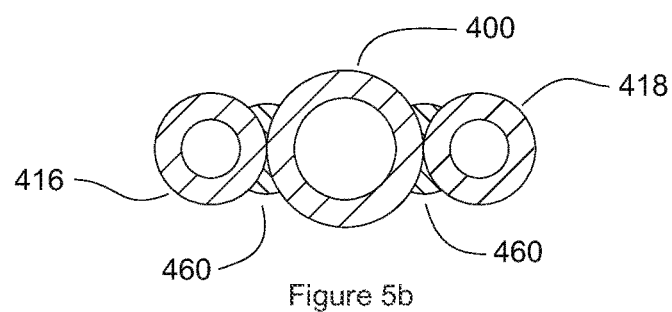

As an alternative to a continuously attached relationship between the respective IV sets, the at least one secondary IV set 416 may be secured to the primary IV set 400 and/or an adjacent secondary IV set 318 in discontinuous fashion by employing discrete points of attachment 460, as illustrated in FIGS. 4b and 5b. In this configuration, the discrete secured segments of the secondary IV sets 416, 418 can be separated by discontinuous, unsecured segments of lengths of the tubular structures making up the IV sets to provide detectable stop points for peeling away the secondary IV sets 416, 418 at predetermined lengths. These stop points provide or define pre-formed lengths of line that can be stripped away upon severing the attachment members, and will allow the user to consciously determine how much of an IV set to strip. As an IV set is pulled free from art adjacent IV set, each point of attachment releases; allowing the user to choose to partially strip the line or to continue progressively breaking each bond until the line is fully removed. One advantage of a partial release is that attending medical personnel can have a length of line now free from the IV set with another part of the line remaining joined. The now free length can be used for a variety of purposes, such as to connect to an additional saline or fluid bag, a medication infusion source, etc. The length of this free segment can be chosen by the attendant as needed.

By having discontinuous, discrete points of attachment spaced along joined IV sets, the unneeded lines can be removed with less applied force. To accomplish this, each attachment member 362 can be bonded or secured at spaced intervals with material that can be easily pulled free from one or more of the joined IV sets, or torn without applying inappropriate breakaway force that could jeopardize the integrity of either of the joined IV sets and/or maintenance of the IV sets in a secure relationship with the patient. In one example, the secondary lines 416, 418 may be secured to the primary line 400 in differing discrete segments having differentially secured lengths to provide offset positions for access points along the length of the primary IV set. This configuration can assist personnel in avoiding the use of competing space for their procedures by having the various access points of each IV set displaced from each other. Regardless of the method of attachment, the IV sets can be configured to break free without undo force so as to not disturb the patient access point. The integrity of the IV sets (leak-free, internal and external wall diameter, longitudinal stretching) can remain unaltered. Although the intention is to allow the IV sets to be stripped away from one another, the construct in which they are attached can be significant enough that they will be able to maintain form without inadvertent stripping.

Figure 6A:
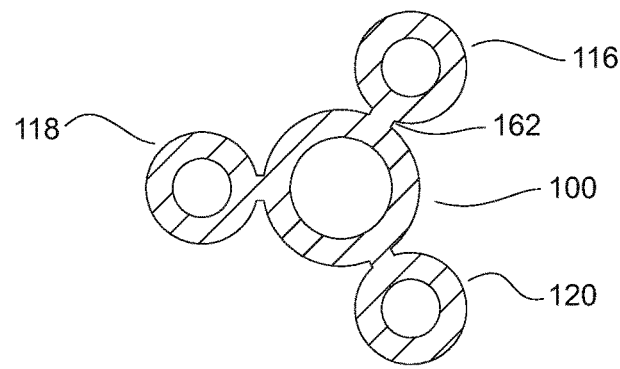
FIG. 6a illustrates a cross-sectional view of an IV set system having the secondary IV sets oriented and arranged with respect to the primary flow line of the primary IV set of the IV set system, in accordance with one exemplary configuration and embodiment of the present invention.
Figure 6B:
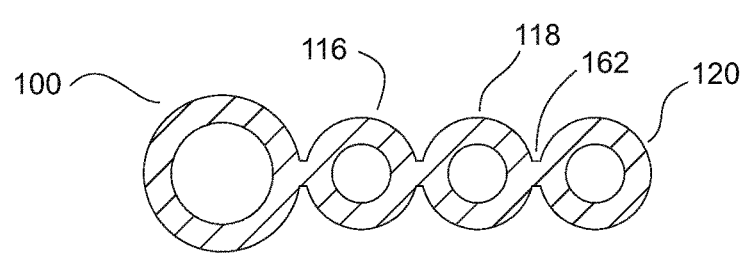
FIG. 6b illustrates a cross-sectional view of an IV set system having the secondary IV sets oriented and arranged with respect to the primary flow line of the primary IV set of the IV set system, in accordance with another exemplary configuration and embodiment of the present invention.

FIGS. 6a and 6b further illustrate how the at least one secondary IV sets can be aligned in either a planar (linear) or a circumferential arrangement with respect to the primary IV set or other attached secondary IV sets. With reference to FIGS. 1 and 6a, secondary IV sets 116, 118 and 120 are shown as being aligned in an exemplary parallel and circumferential arrangement with respect to the primary IV set 100. In this example, the primary IV set 100 comprises a larger diameter that facilitates the attachment of the secondary lines 116, 118 and 120 axially around the primary IV set 100 in parallel fashion, such as from proximal to distal termini. With reference to FIGS. 1 and 6h, the secondary IV sets 116, 118 and 120, and the primary IV set 100, are shown as being aligned in an exemplary planar or linear arrangement in relation to the primary IV set 100, and in parallel fashion, such as from proximal to distal termini.

The choice of alignment can depend upon several factors. The planar or linear arrangement allows for a low profile. A low profile can be very desirable when the IV set may come in contact with another object (e.g., arms tucked at the patients side in the OR, patient in a lateral position in the OR, etc.) This particular design does, however, restrict the care provider from stripping away the interior secondary IV set of the inter-attached bundle of IV sets as it will be in contact with both the primary IV set and other secondary IV sets. (See FIG. 6b) The circumferential arrangement shown in FIG. 6a provides attending medical personnel more options over the arrangement in FIG. 6b in regards to stripping away IV sets and customization. This arrangement does, however, increase the profile of the IV set system. FIGS. 6a and 6h further illustrate attachment members 162 separably coupling the primary IV set 100 with the one or more secondary IV sets 116, 118, and 120.

In addition to the structural features set forth above, several options for applying a disclosed method for using the strippable IV set with integrally attached flow lines are illustrated below. Those persons skilled in the art will identify various methods and applications for the featured structural embodiments set forth; however, several general procedures are specifically set forth. For example, the present invention includes a method for managing use of a primary IV set and multiple, integrally and removably inter-attached secondary IV sets of a bundled IV set system to minimize entanglement of the lines of the IV sets during use. This method can be generally described by the steps of a) initiating application of the IV set system to a patient in a customary manner using a primary flow line of a primary IV set. This may be a carrier fluid such as saline or any other appropriate fluid medium. A second step (b) would be identifying a first secondary IV set of the bundled IV set system for administering a second substance to the patient, such as a medication, and then at least partially stripping an upper end of the first secondary IV set from the primary IV and or a secondary IV set to provide a free, unattached end of the first secondary IV set. This free end facilitates proper access and positioning of the line with respect to the IV set system in an organized manner, while retaining an attached portion integral with the bundled IV sets to avoid entanglement with other IV sets. As an additional step (c), a second secondary IV set may also be identified for administering a third substance to the patient, such as a sedating or anesthetizing agent. In a similar manner as with the first secondary IV set, an upper end of this second secondary IV set is at least partially stripped to provide a free, unattached end to facilitate proper access and positioning thereof with respect to the IV set system, while retaining the attached portion of the line integral with the IV set, thereby reducing likelihood of entanglement of this line. A further step (d) involves stripping lower ends of these secondary lines from one or more IV sets within the IV set system, and then coupling them to access ports at the lower distal portion of the primary IV set, such as via the merging fluid pathway. These first and second lines can then be coupled to appropriately administer solutions. When marked with unique indicia, each line can be clearly identifiable and quickly accessible to attending medical personnel. If desired, the attendant may completely strip at least one of the first or second secondary IV sets free from the IV set system when one or more of those sets are no longer required, thus further simplifying the IV set system and reducing likelihood of entanglement with other lines. In this case indicia matching indicia from that stripped IV set can remain or caused to be visible on the primary IV set.

Multiline Manifold Attachment

In many settings throughout the hospital, healthcare providers often have a need to quickly administer boluses of multiple medications. This need may stem from patient condition, current procedure or both. This challenge is often met through the use of an injection port manifold, which consists of multiple injection ports organized in close proximity. Standard manifolds are part of the fluid pathway enabling injections to be carried from the injection on the manifold site to the IV patient connection. Manifold injection ports often contain a unidirectional flow apparatus enabling syringes to be left in connection to the port without fluid backflow into the syringe. Manifolds an also be composed of two or more stopcocks permanently attached to one another.

The settings of the hospital are where an anesthesia providers practice are especially prone to manifold utilization. Induction of anesthesia requires the bolus injection of various medications in rapid succession. The timing of medication administration during the induction of anesthesia coincides with the need for the anesthesia provider to externally maintain the patient's airway and ventilation. This need makes the use of a manifold especially helpful because it enables the provider to inject medication at the manifold with one hand.

Current IV manifold sets are often bulky making their presence undesirable in settings where their use is not needed. To overcome this challenge, other current manifolds are often connected in-line with the primary IV set utilizing, for example, an alternating male/female Luer Lock system enabling the in-line manifold to be removed and the remaining primary IV set to be reattached. An important disadvantage of this in-line arrangement or configuration is the requirement to "break" or completely separate the fluid pathway, thus increasing the risk of contaminating the IV line and increasing the risk for infection. Manifolds are often used during the anesthesia portion of the hospital stay and are then removed upon transfer of the patient to other areas of the hospital.

The IV set system of the present disclosure can further comprise a manifold design that provides solutions to the problems discussed above. The unique manifold design of the present disclosure overcomes problems of current manifolds by being mounted externally to the primary IV set, thus establishing a bypass flow line to the segment of primary line where it is attached, such as a segment of the primary flow e. This bypass design serves to create an alternate primary flow path to the primary flow line through the manifold and the bypass flow line that is outside of or out of line from the regular primary flow path in the primary flow line, that facilitates administration of multiple boluses through the manifold either by injection or other acceptable means. By directly delivering the bolus into the primary line carrier fluid, fluid trapping within the manifold is prevented, ensuring that the entire bolus is delivered to the patient. This externally mounted manifold bypass design will allow for the manifold to be added to the primary IV set by the attending medical personnel whenever it is deemed necessary and will further allow the manifold to be removed when its presence is unwanted or no longer needed.

Figure 7A:
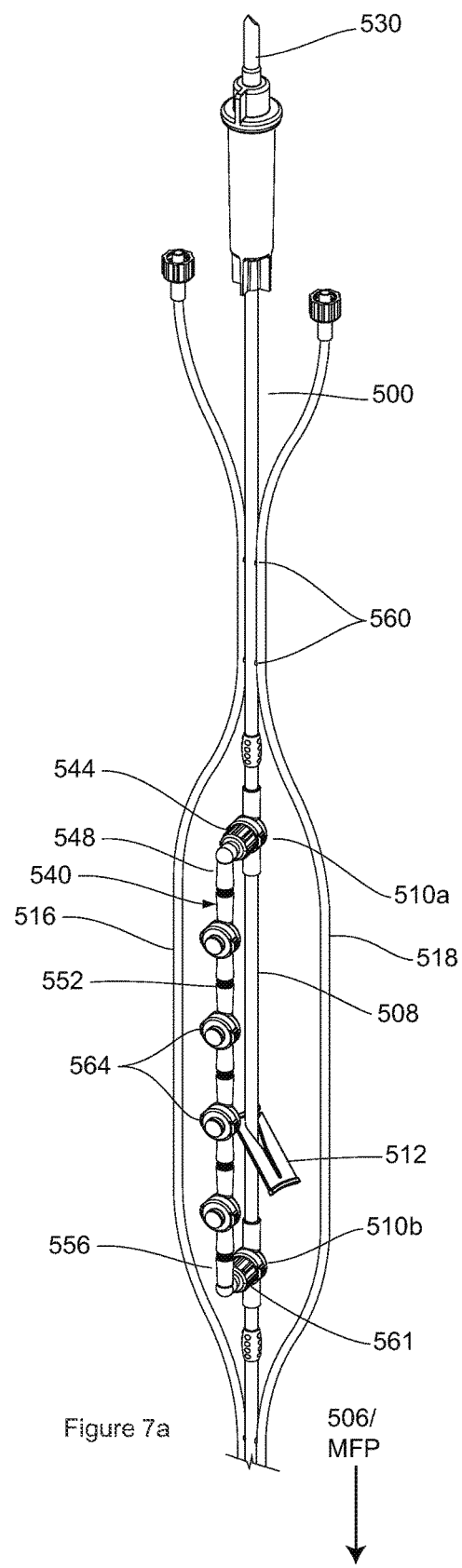
FIG. 7A illustrates a partial plan view of an IV set system having a manifold bypass device in use with a primary flow line of a primary IV set, in accordance with one exemplary embodiment of the present invention.

With reference to FIG. 7A, illustrated is an IV set system having a primary 500, a primary flow line 508, and secondary lines 516 and 518, these being similar in form and function to those described above. The IV set system of FIG. 7A can further comprise marking indicia, separably joined IV sets (such as via attachment members 560), and a merging fluid pathway as set forth and described in any of the embodiments discussed herein, as will be recognized and as can be applied by one of ordinary skill in the art.

The IV set system further comprises a manifold 540 operable with the primary IV set 500, in accordance with one example of the present disclosure. Access ports 510 on the primary IV set 500 can be used to removably and externally couple the manifold 540 in a lateral manner relative to the primary IV set 500. The manifold 540 can be prefabricated into or otherwise formed and made operable with the primary flow line 508. Access ports 564 (e.g., n number of access ports) for use with syringes, secondary IV sets and other possible supporting flow lines can be formed or provided in the manifold 540 in a similar manner as the access ports 510 formed in the primary IV set 500. The primary IV set 500 can further comprise access ports 510, some of which can be referred to as manifold access ports, that are operable to removably couple corresponding access points on the manifold 540. In the embodiment shown, access ports 510a and 510b function as the access ports on the primary IV set 500 used to laterally couple the manifold 540. The access points on the manifold 540 can comprise threaded port adaptors or other connector types 544 and 561 that removably couple to the access ports 510a (manifold input access port) and 510b (manifold output access port), respectively. The access points on the manifold 540 can be spaced apart to match the respective positions of the access ports 510a and 510b on the primary IV set 500. In this embodiment, the attending medical personnel can make a spontaneous decision to apply a manifold bypass flow line if it is needed. No structural adaptation of the IV set system is required, other than clipping or otherwise coupling the manifold device 540 to the respective access ports 510 on the primary line 500, and particularly the primary flow line 508. Similarly, the manifold 540 can be disconnected when the bypass flow line is no longer needed; wherein fluid flow through the primary flow line of the primary IV set 500 is restored. The bypass design also eliminates the requirement to "break" or completely disconnect the IV set system, thus reducing the contamination and infection risk. Accordingly, the adaptation of the primary flow line with a manifold bypass attachment structure greatly enhances both convenience and safety, as compared with prior art practices utilizing an inline manifold configuration. In one aspect, the manifold 540 can be prefabricated.

For most patients a hospital encounter is a multi-departmental experience. As a patient travels from one department to another, patient needs and provider focuses change. The present IV set system allows easy transition from one department to the next and adapts to changing patient needs and staff requirements important advantage of the present IV set system and its removably coupleable bypass manifold 540 over current manifold systems is the referenced ability to spontaneously add and remove the manifold 540 to/from the IV flow path or fluid pathway without interrupting or interfering with IV function, and particularly the primary flow path, making it readily adaptable to most patient settings. For example, a trauma patient who is transported to the hospital by ambulance may require the ambulance crew to quickly establish IV access using a present IV set system. Upon arrival at the hospital, the present IV set system could then be utilized by emergency department personnel to administer medications, and fluids. Up to this point the presence of a manifold may be unnecessary and the added bulk to the line set could increase the risk of the IV becoming caught, tangled or pulled out during patient transfers. However, many patients in the emergency department are transferred directly to the operating department for treatment. For reasons previously described, anesthesia providers often prefer the use of manifolds. With use of the present IV set system, the anesthesia or other provider could simply and quickly couple a present manifold 540 to an IV set as needed or desired, thus creating a bypass flow line that effectively reroutes or diverts the fluid pathway already established, without breaking it. In other words, the manifold facilitates diverting of the fluid from the primary flow line through the manifold and the bypass flow line to form an alternate primary fluid flow path, wherein the flow of the fluid is maintained in a continuous manner and not stopped. Alternatively, and in some instances, it may be desirable to have the IV set system preconfigured with the bypass manifold 540 pre-attached and ready to use. Otherwise, as indicated, upon arrival to the operating department the anesthesia or other provider could attach the externally mountable manifold 540 to the access ports of the IV set system without "breaking" the IV flow-path. The manifold 540 could be utilized during the pre-operative and operative periods, and removed prior to the patient's transfer to the post-operative, intensive care or medical/surgical unit. A comparative example would be a patient scheduled for an inpatient surgical procedure. The patient, upon arrival at the pre-surgical area, could routinely have IV access established. The preoperative nurse could select an IV set system, as described herein, with a manifold 540 pre-attached allowing the manifold 540 to be utilized during induction and maintenance of anesthesia. The manifold 540 could then be safely and easily removed at the end of the operative period, prior to transferring the patient to the designated post-surgical department. The self-sealing access ports 510a and 510b could be used as regular access ports in the absence of the manifold 540.

The IV set system can further comprise a flow control valve or device associated with the primary flow line of the primary IV set. The flow control valve can operate to selectively divert fluid flow from the primary flow line to the manifold and through the bypass flow line to form the alternate primary flow path, and then to restore fluid flow through the primary flow line of the primary IV set, such as upon removal of the manifold from the primary IV set. In one aspect, the flow control valve can comprise a clamp, such as a slide clamp, a roller clamp, etc. In another aspect, the flow control valve can comprise a stop cock on a proximal connection point on the primary line.

At a predetermined distance distal to the infusion spike 530 and proximal to the distal most access point of the primary IV set 500 and secondary IV sets 516, 518, two threaded self-sealing access ports 510a and 510b can be placed continuous and in fluid communication with the primary flow line 508 and the primary flow path. The predetermined distance (as measured between the lower of the access ports connecting the manifold (e.g., 510b) and the distal most access point of the primary IV set 500) can be, for example, between one and five feet. In one aspect, this distance can be three feet.

The access ports 510a, 510b can be spaced at a predetermined distance from each other and, in some examples, can be part of a connector portion oriented at a substantially 90-degree or orthogonal orientation relative to the primary line 500. In one example, the access ports 510a and 510b can be part of a connector portion oriented on a 90 degree or orthogonal orientation and can comprise a female portion of a Luer Lock, with the connectors 544 and 561 on the manifold 540 comprising male portions of a Luer Lock formed on a 90 degree orientation relative to the primary flow line and operable to couple to the female portions of the Luer Lock. Other connection types or systems are contemplated herein, and one skilled in the art will recognize that a Luer Lock type connection system is not intended to be limiting in any way. In one example the manifold 540 can comprise first and second connector portions of the same type, such as male-male or female-female. In other words, the connector portion types on the manifold 540 designed to couple with the access ports on the primary IV set can be the same, each being operable to couple to the access ports in the same manner. This is unlike prior manifold designs that are coupled in an in-line configuration with the primary flow line where the connectors or connector types are alternating.

Figure 7B:
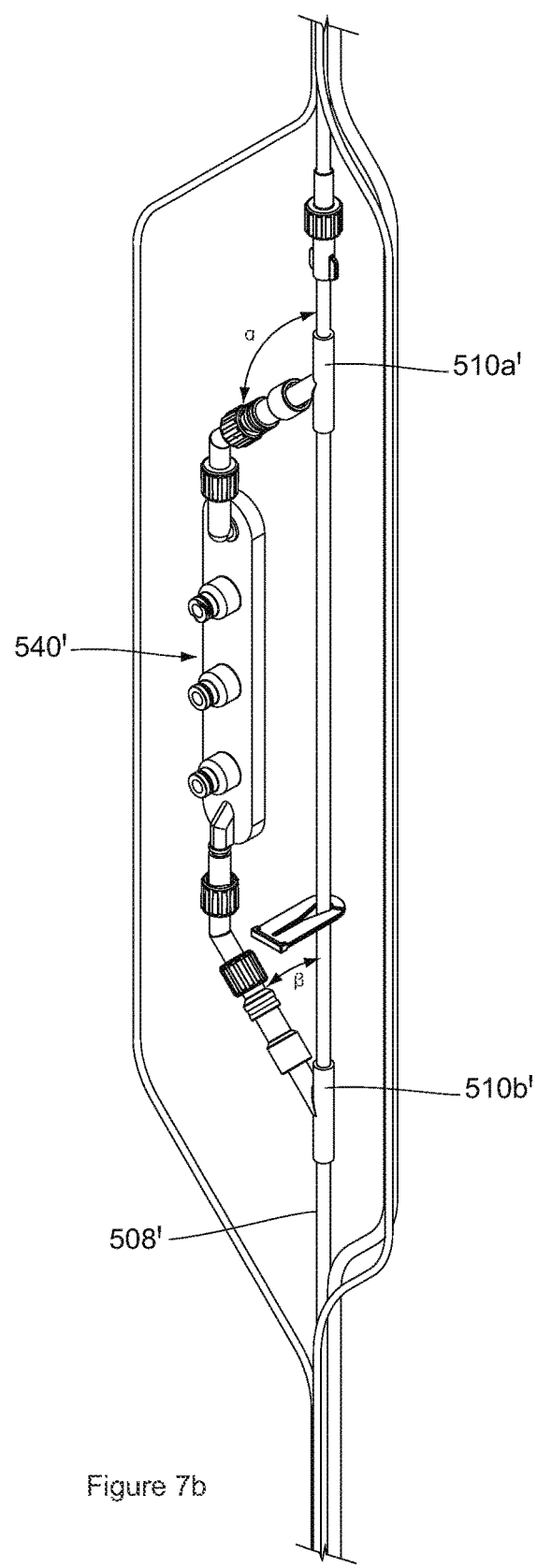
FIG. 7B illustrates a partial plan view of the IV set of FIG. 7A, the IV set comprising a manifold configuration in accordance with an exemplary alternative configuration.
Figure 7C:
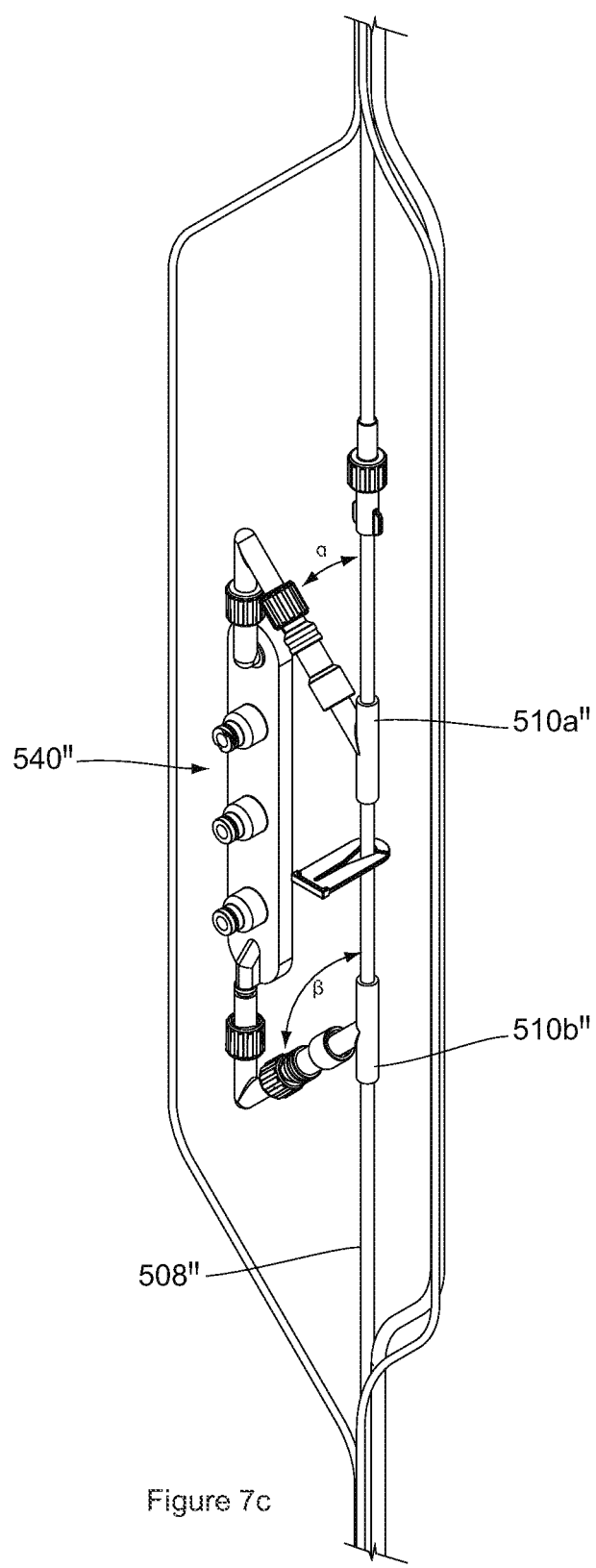
FIG. 7C illustrates a partial plan view of the IV set of FIG. 7A, the IV set comprising a manifold configuration in accordance with still another exemplary alternative configuration.

As one skilled in the art will recognize, connection systems having angular orientations other than 90 degrees may be employed and used where merited by the circumstances, such as connector portions having angular orientations between 30 and 150 degrees (as measured from the longitudinal axis of the primary line 500), or even others. For example, FIG. 7B illustrates access ports 510a' and 510b', each being formed as part of a connector portion oriented on an angle other than 90 degrees relative to the primary flow line 108'. Specifically, access port 510a' forms part of a connector portion oriented in a downward direction on an angle α (e.g., 120 degrees), and access port 510b' forms part of a connector portion that is oriented in an upward direction at an angle fi (e.g., 30 degrees). In another example, FIG. 7C illustrates access ports 510a" and 510b", each being formed as part of a connector portion oriented on an angle other than 90 degrees relative to the primary flow line 108". Specifically, access port 510a" forms part of a connector portion oriented in an upward direction at an angle α (e.g., 30 degrees), and access port 510b" forms part of a connector portion that is oriented in downward direction at an angle β (e.g., 120 degrees). As can be seen, and as will be appreciated by those skilled in the art, the relative degrees of angles α and β of the access ports in the above examples of FIGS. 7A-7C can range anywhere between 0 and 180 degrees).

Referring back to FIG. 7A, a flow control valve or device in the form of a slide style clamp 512 can be placed on the primary line 500 between the two access ports 510a and 510b. A threaded port adapter or other connector 544 on the manifold 540 can be connected to the proximal access port 510a and can be oriented perpendicular or orthogonal to the primary flow line 508. The port adapter 544 can then be connected to a solid 90-degree angle or other angular orientation connector 548 on the manifold 540, which can divert the flow path through the manifold 540 in a direction parallel to the primary flow line 508 of the primary IV set 500. The flow can continue distal to the 90-degree or other angular orientation connector 548 along a solid manifold or bypass line 552 (e.g., the bypass flow line), which can continue parallel to the primary IV set 500. The solid manifold or bypass line 552 can comprise one or more access ports 564 that function similar to the access ports 510 on the primary IV set 500.

Lateral to the distal self-sealing access port 510b can be a second 90-degree or other angular orientation connector 556 on the manifold 540 attached to the primary IV set 500 via a threaded port adaptor or other connector 561 that can be connected to the distal self-sealing access port 510b of the primary IV set 500. When the manifold 540 is connected to the primary IV set 500, the slide clamp 512 can be closed to occlude the primary flow line 508 in-between the two self-sealing access ports 510a and 510b. This will divert flow from the primary flow line 508, through the proximal self-sealing access port 510a and through the manifold 540, thus creating or forming an alternate primary fluid flow path. The flow can then continue through the manifold or bypass flow then through the distal self-sealing access port 510b and then back into the primary flow line where it will continue through the distal portion of the primary flow line 508 until it terminates at the IV patient interconnect. When the manifold 540 is not needed it can be removed and the slide clamp 512 opened to allow direct flow through the primary flow line 508.

The advantages of the present manifold and the formed bypass over the prior art are significant. The ability to add and remove the manifold will allow Dora quick, safe and effective method of patient centered, interdepartmental IV adaptation. This adaptability will reduce the need to change the entire IV set system as the patient's treatment, department, or status changes. This can result in a decrease in treatment costs and medical waste. Addition and removal of the manifold can be done by entering, but not separating the primary flow path. This will increase patient safety by reducing the risk of exposure to contaminants or infective agents during addition or removal of the manifold apparatus.

It will be apparent to those skilled in the art that the present invention can be viewed as a total or complete IV system in which the components and features discussed herein, in any of the embodiments, can be combined and cooperate together to provide an IV set system having a level of safety, performance, and convenience within the medical field, unlike current, mere compilations of IV sets. For instance, an exemplary intravenous (IV) set system can comprise, in combination, a primary IV set having a plurality of access points facilitating access to one or more fluid pathways of the primary IV set, and top-level marking indicia; a secondary IV set removably coupleable with the primary IV set via one of the access points of the primary IV set, the secondary IV set comprising a plurality of access points facilitating access to one or more fluid pathways of the secondary IV set, and marking indicia that differs from the top-level marking indicia of the primary IV set, wherein the primary and secondary IV sets are distinguishable from one another, wherein the secondary IV set is further separably joined to the primary IV set in at least a semi-continuous manner substantially alone: its length to inhibit entanglement with the primary IV set, and wherein the secondary IV set is at least partially strippable from the primary IV set; a manifold operable to externally removably couple to the primary IV set via the plurality of access points, the manifold comprising a bypass flow line forming an alternate primary flow path to a fluid pathway of the primary IV set; a merging fluid pathway located about the primary IV set and comprising one or more access ports, wherein the at least one secondary IV set is fluidly coupleable to one of the access ports of the merging fluid pathway, such that a fluid flow path of the secondary IV set merges with a fluid flow path of the primary IV set.

The IV set system of the present invention as discussed herein provides interactive and synergistic features that offer a significant step forward over prior IV sets or compilations of IV sets. Furthermore, each inventive component as described above can be viewed as a separate invention that can be applied within other fields of use independent of the whole. Several examples of such allocations and procedures have been set forth above and need no further explanation.

The foregoing structures and descriptions can also be applied with respect to procedures and methods of administering an IV to a patient with the benefit of reducing risk of error. Specifically, the method provides selective identification of at least one IV set defining at least one flow line within an IV set system which includes (i) a primary IV set having a proximal terminus, a distal terminus, and an intermediate tubular length defining a primary flow line of the primary IV set and (ii) at least one secondary IV set defining at least one secondary flow line configured to feed to the primary flow line of the primary IV set, the at least one secondary IV set having a proximal terminus, a distal terminus, and an intermediate tubular length. The representative steps of the method can include (a) applying at least one common set of unique marking indicia, which can also be uniform, to at least one of the primary and/or secondary IV sets to enable rapid identification thereof with respect to other lines of the IV set system; and (b) allocating or associating the at least one primary and/or secondary IV sets having the unique marking indicia to/with a primary function or primary user as part of a medical procedure, thereby providing notice to other attending medical personnel of the allocated function for the at least one primary IV set and/or secondary IV sets. Several examples of such allocations and procedures have been set forth above and need no further explanation.

The following examples illustrate several options for applying the disclosed features in greater detail. For example, the method may further comprise the steps of (i) applying the unique marking indicia (which may also be uniform) to a plurality of access points/ports positioned along the primary IV set of the IV set system to identify the primary IV set from other lines of the IV set system, and (ii) allocating the primary flow line with the function of providing the IV with a primary carrier fluid flow line. Furthermore, secondary IV sets may also be marked and identified in a similar manner. For example, the method may also include the steps of (i) applying the unique marking indicia (which may also be uniform) to at least one of the secondary IV sets, including at least the distal terminus of the secondary IV set, for identification thereof from other lines of the IV set system and (ii) allocating the secondary flow line to the function of providing an infusion flow path into the primary flow line.

It will be apparent that the IV set system and the methods of administering a patient IV disclosed above can be practiced in numerous combinations with selective identification of some or all IV sets of the IV set system being appropriately marked to facilitate identification of selected IV sets through multiple stages of patient care.

A further a general method is disclosed for providing access for bolus injections and/or secondary IV sets to a primary flow line of a primary IV set using an external bypass manifold having at least one access port. This step can be taken without breaking the primary fluid flow line of the primary IV set and the fluid flow to a patient, hut rather by diverting such primary fluid flow. The steps of this procedure can include a) coupling a first proximal end of the manifold to a segment of the primary IV set through an access port on the primary IV set that communicates directly with the primary flow line and the fluid flow path the therein. The method can further comprise b) positioning the manifold adjacent to and aligned with the segment of the primary IV set, and c) coupling the second distal end of the manifold to the segment of the primary IV set through another access port on the primary IV set that also communicates directly with the primary flow line and the fluid flow path therein. Laterally coupling the manifold in this manner effectively establishes a bypass flow line external and adjacent to the primary flow line (e.g., out of line rather than in-line) of the primary IV set. The method can further comprise d) blocking flow through the primary flow line within the segment of the primary IV set, thereby diverting fluid flow and the fluid flow path through the bypass line created by the manifold. The method can further comprise e) coupling a fluid delivery device, such as a syringe or a secondary line, to an access port of the manifold to enable fluid flow into the manifold bypass line, such as to administer fluids (e.g., medication, analgesics, etc.) to the patient.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in art embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the all that numerous modifications in form, usage and details of implementation can be made without the exercise of inventive faculty, and without departing from the principles and concepts of the invention.

The invention claimed is:
1. An intravenous (IV) set system, comprising:
a primary IV set having a plurality of access points facilitating access to one or more fluid pathways of the primary IV set, at least some of the access points comprising access ports providing fluid access to a primary flow line of the primary IV set; and
a manifold externally coupled to the primary IV set via at least some of the access ports of the primary IV set, the manifold comprising a bypass flow line adjacent the primary flow line, and one or more access points that facilitate access to the bypass flow line, wherein the manifold and the bypass flow line provide an alternate primary flow path to a primary flow path through the primary flow line.

2. The IV set system of claim 1, further comprising a flow control valve operable to selectively divert fluid flow from the primary flow line to the manifold and through the bypass flow line.

3. The IV set system of claim 1, further comprising a secondary IV set removably couple able with the primary IV set via one of the access points of the primary IV set, the secondary IV set comprising a plurality of access points facilitating access to one or more fluid pathways of the secondary IV set.

4. The IV set system of claim 1, wherein the manifold provides the bypass flow line and establishes the diverted fluid without breaking the fluid flow.

5. The IV set system of claim 1, wherein the primary flow line and the bypass flow line are in fluid communication with one another.

6. The IV set system of claim 1, wherein the manifold is coupled to the primary IV set at a location proximate a distal terminus of the primary IV set.

7. The IV set system of claim 1, wherein the flow control valve comprises a clamp located on the primary flow line.

8. The IV set system of claim 1, wherein the flow control valve comprises a stop cock on a proximal connection point on the primary line.

9. The IV set system of claim 1, wherein the manifold comprises first and second connector portions that fluidly couple to the access ports of the primary IV set, the bypass flow line being in fluid communication with the primary flow line.

10. The IV set system of claim 9, wherein the first and second connector portions comprise the same connector portion type, each being operable to couple to respective access ports in the same manner.

11. The IV set system of claim 9, wherein the first and second connector portions each comprise a male type connector portion, and wherein at least some of the access ports on the primary IV set form part of a female type connector portion operable to couple with the male type connector portions.

12. The IV set system of claim 1, wherein at least one of the access ports on the primary IV set forms part of a connector portion oriented orthogonally relative to the primary flow line of the primary IV set, and wherein the manifold comprises at least one connector portion oriented orthogonally relative to the primary flow line to connect with the access ports on the primary IV set.

13. The IV set system of claim 1, wherein at least one of the access ports on the primary IV set forms part of a connector portion oriented on an incline relative to the primary flow line of the primary IV set, and wherein the manifold comprises at least one connector portion oriented on an incline relative to the primary flow line to connect with the access ports on the primary IV set.

14. The IV set system of claim 1, wherein the manifold is coupled to the primary IV set at a distance, as measured from a distal most access point on the primary IV set, between 1 and five feet.

15. The IV set system of claim 1, wherein the primary IV set comprises top-level marking indicia that functions to distinguish the primary IV set, wherein the top-level marking indicia are associated with one or more of the access points of the primary IV set.

16. The IV set system of claim 1, further comprising at least one secondary IV set operable with the primary IV set.

17. The IV set system of claim 16, wherein the secondary IV set comprises marking indicia that differs from a top-level marking indicia of the primary IV set, and wherein the primary and secondary IV sets are distinguishable from one another.

18. The IV set system of claim 16, wherein the primary IV set further comprises second-level marking indicia, wherein the second-level marking indicia of the primary IV set matches the marking indicia of the secondary IV set providing a set of matching indicia across IV sets.

19. The IV set system of claim 18, wherein the top-level and second-level marking indicia of the primary IV set are associated with at least one access point of the primary IV set, and wherein the marking indicia of the secondary IV set is associated with at least one access point of the secondary IV set.

20. The IV set system of claim 16, wherein the at least one secondary IV set is separably joined with the primary IV set in at least a semi-continuous manner substantially along its length to inhibit entanglement with the primary IV set.

21. The IV set system of claim 20, wherein the secondary IV set is at least partially strippable from the primary IV set.

22. The IV set system of claim 16, wherein another secondary IV set is separably joined with the at least one secondary IV set in at least a semi-continuous manner substantially along its length to inhibit entanglement with the at least one secondary IV set and the primary IV set.

23. The IV set system of claim 1, further comprising a merging fluid pathway situated proximate a distal terminus of the primary IV set, the merging fluid pathway providing direct access to a fluid pathway of the primary IV set via one or more access ports.

24. An intravenous (IV) set system, comprising:
a primary IV set having a plurality of access points facilitating access to one or more fluid pathways of the primary IV set, at least some of the access points comprising access ports providing fluid access to a primary flow line of the primary IV set;
a manifold externally coupled to the primary IV set via at least some of the access ports of the primary IV set, the manifold comprising a bypass flow line adjacent the primary flow line forming an alternate primary flow path, and one or more access points that facilitate access to the bypass flow line,
wherein the manifold comprises first and second connector portions of the same type, the access ports and the connector portions being oriented on an angle relative to the primary flow line.

25. The IV set system of claim 24, wherein the first and second connector portions each comprise a male type connector portion, and wherein at least some of the access ports on the primary IV set form part of a female type connector portion operable to couple with the male type connector portions.

26. The IV set system of claim 24, wherein the access ports and the connector portions are oriented on an angle relative to the primary flow line between 0 and 180 degrees.

27. The IV set system of claim 24, wherein the access ports and the connector portions are oriented on an angle relative to the primary flow line of 90 degrees.

28. A method for bypassing a primary flow path of a primary flow line within a primary IV set, the method comprising:
obtaining a primary IV set having a plurality of access points facilitating access to one or more fluid pathways of the primary IV set, at least some of the access points comprising access ports providing fluid access to a primary flow line of the primary IV set;

diverting fluid from the primary flow line to a bypass flow line of a manifold removably and externally coupled to the primary IV set via the access ports, the manifold comprising one or more access points that facilitate access to the bypass flow line; and providing, through the manifold, an alternate primary flow path to a primary flow path through the primary flow line.

29. The method of claim 28, further comprising selectively actuating a flow control valve operable to selectively occlude fluid flow through the primary flow line of the primary IV set and to divert the fluid through the manifold and the bypass flow line.

30. The method of claim 28, further comprising restoring fluid flow through the primary flow line of the primary IV set.

\* \* \* \* \*

UNITED STATES PATENT AND TRADEMARK OFFICE
CERTIFICATE OF CORRECTION

PATENT NO. : 9,833,560 B2
APPLICATION NO. : 14/458229
DATED : December 5, 2017
INVENTOR(S) : Lucas Reichert et al.

It is certified that error appears in the above-identified patent and that said Letters Patent is hereby corrected as shown below:

In the Claims

Column 31, Line 23, of claim "1" should read of claim --2--

Column 31, Line 25, of claim "1" should read of claim --2--

Signed and Sealed this
Twenty-third Day of April, 2019

Andrei Iancu
*Director of the United States Patent and Trademark Office*